US006429302B1

(12) United States Patent
Kennedy

(10) Patent No.: US 6,429,302 B1
(45) Date of Patent: Aug. 6, 2002

(54) POLYNUCLEOTIDES RELATED TO PANCREATIC DISEASE

(75) Inventor: Giulia Kennedy, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/490,818

(22) Filed: Jan. 25, 2000

Related U.S. Application Data

(60) Provisional application No. 60/118,302, filed on Feb. 2, 1999.

(51) Int. Cl.[7] .................. C07H 21/02; C07H 21/04; G01N 33/48
(52) U.S. Cl. .................. 536/23.5; 436/64; 536/23.1
(58) Field of Search .............................. 536/23.1, 23.5; 436/64

(56) References Cited

U.S. PATENT DOCUMENTS

| | | |
|---|---|---|
| 5,445,934 A | 8/1995 | Foder et al. |
| 5,776,683 A | 7/1998 | Smith et al. |
| 5,800,992 A | 9/1998 | Fodor et al. |
| 5,807,680 A | 9/1998 | Sutcliffe et al. |

FOREIGN PATENT DOCUMENTS

| | | |
|---|---|---|
| WO | WO 95/35505 | 6/1995 |

OTHER PUBLICATIONS

Reiger et al Glossary of Genetics and Cytogenetics, Classical and Molecular, 4th Ed., Springer–Verlay, Berlin, 1976.*
Burgess et al., J of Cell Bio. 111:2129–2138, 1990.*
Lazar et al. Molecular and Cellular Biology 8:1247–1252, 1988.*
Bowie et al. Science, 247:1306–1310, 1990, p. 1306, col. 2.*
Waterstone, R., Genbank Sequence Database (Accession HSAC000064), National Center for Biotechnology Information, National Library of Medicine, Bethesda, Maryland, publicly available Nov. 13, 1996.*
Tone et al., Genbank Sequence Database (Accession S82420S1), National Center for Biotechnology Information, National Library of Medicine, Bethesda, Maryland, publicly available Dec. 3, 1996.*
Merrill et al., Genbank Sequence Database (Accession Q32834), National Center for Biotechnology Information, National Library of Medicine, Bethesda, Maryland, publicly available May 5, 1993.*
Hillier et al. (1996) "Generation and analysis of 280,000 human expressed sequence tags" Database EMBL.
Pauley (1996) "The sequence of H. Sapiens BAC clone RG083M05" Database EMBL.
Genbank Accession No. AC005230, deposited Sep. 30, 2000.

Genbank Accession No. AC007566, deposited Nov. 16, 2000.
Genbank Accession No. AK026142, deposited Sep. 29, 2000.
Genbank Accession No. AL122008, deposited Mar. 6, 2001.
Genbank Accession No. AL359092, deposited Mar. 17, 2001.
Bramhall (Apr. 1998), "The Use of Molecular Technology in the Differentiation of Pancreatic Cancer and Chronic Pancreatitis," *Intl. J. of Pancreatology*, vol. 23(2):83–100.
Carter (1990), "Cancer of the Pancreas," *Gut*, vol. 31:494–496.
DeRisi et al., (Dec. 1996), "Use of cDNA Microarray to Analyse Gene Expression Patterns in Human Cancer," *Nature Genetics*, vol. 14:457–460.
DeRisi et al. (Oct. 1997), "Exploring the Metabolic and Genetic Control of Gene Expression on a Genomic Scale," *Science*, vol. 278:680–686.
Del Villano et al. (1983), "Radioimmunometric Assay for Monoclonal Antibody–Defined Tumor," *Clin. Chem.*, vol. 29(3):549–552.
Drmanac et al. (Jun. 1993), "DNA Sequence Determination by Hybridization: A Strategy for Efficient Large–Scale Sequencing," *Science*, vol. 260:1649–1652.
Everhart et al. (May 24/31, 1995), "Diabetes Mellitus as a Risk Factor for Pancreatic Cancer," *JAMA*, vol. 273(20):1605–1609.
Fabris et al. (1988), "Serum Markers and Clinical Data in Diagnosing Pancreatic Cancer: A Contrastive Approach," *American Journal of Gastroenterology*, vol. 83(5)549–553.
Frebourg et al. (1988), "The Evaluation of CA 19–9 Antigen Level in the Early Detection of Pancreatic Cancer," *Cancer*, vol. 62:2287–2290.
Friess et al. (1997), "Molecular Versus Conventional Markers in Pancreatic Cancer," *Digestion*, vol. 58:557–563.

(List continued on next page.)

*Primary Examiner*—Anthony C. Caputa
*Assistant Examiner*—Gary B. Nickol
(74) *Attorney, Agent, or Firm*—Carol L. Francis; Kimberlin L. Morley; Robert P. Blackburn

(57) ABSTRACT

The present invention is based on the discovery of polynucleotides that represent novel genes that are differentially expressed in pancreatic disease, e.g., pancreatic cancer, dysplasia, pancreatitis, or diabetes. The invention features methods of identifying cells affected by such pancreatic diseases by detection of a gene product encoded by such differentially expressed genes, as well as methods of modulating expression of such gene products to effect therapy (e.g., to decrease growth and/or affect abnormal characteristics of cancerous or dysplastic pancreatic cells.)

6 Claims, No Drawings

OTHER PUBLICATIONS

Homma et al. (1991), "The Study of the Mass Screening of Persons Without Symptoms and of the Screening of Outpatients with Gastrointestinal Complaints or Icterus for Pancreatic Cancer in Japan, Using CA 19–9 and Elastase–1 or Ultrasonography," *Int. J. Pancreatol.*, vol. 9:119–124.

Lemoine (1997), "Molecular Advances in Pancreatic Cancer," *Digestion*, vol. 58:550–556.

Ramsay (Jan. 1998), "DNA Chips: State–of–the Art," *Nature Biotechnology*, vol. 16:40–44.

Rhodes et al. (Dec. 1990), "Serum Diagnostic Tests for Pancreatic Cancer," *Baillière's Clinical Gastroenterology*, vol. 4(4):833–851.

Ritts et al. (1984), "Initial Clinical Evaluation of an Immunoradiometric Assay for CA 19–9 Using the NCI Serum Bank," *Int. J. Cancer*, vol. 33:339–345.

Satake et al. (1990), "A Clinical Evaluation of Various Tumor markers for the Diagnosis of Pancreatic Cancer," *Int. J. Pacreatol.*, vol. 7:25–36.

Satake (1991), "Diagnosis of Pancreatic Cancer," *Int. J. Pacreatol.*, vol. 9:93–98.

Schena et al. (Oct. 1995), "Quantitative Monitoring of Gene Expression Patterns with a Complementary DNA Microarray," *Science*, vol. 270:467–470.

Steinberg (1990), "The Clinical Utility of the CA 19–9 Tumor–Associated Antigen," *American Journal of Gastroenterology*, vol. 85(4):350–355.

* cited by examiner

SEQUENCE LISTING

<160> NUMBER OF SEQ ID NOS: 6

<210> SEQ ID NO 1
<211> LENGTH: 676
<212> TYPE: DNA
<213> ORGANISM: Homo sapiens

<400> SEQUENCE: 1
agacaagagt ctcactctgt tgcccaggct ggagcacagc ggtgcaatct tggctcacta      60
caacctccac ctcctgggtt taggcgattc tcctgcctca gcctcctaaa tagctgggat     120
tacaggcaca tgccaccaca cctggctaat tttttgtattt ttagtagcga cggggtttcg     180
ccatgttggc caggctggtc tcgaactcct gacctcaggc gatccacttc ccgacctcag     240
gtgatccgcc tgcctcggcc tctaaaagtg ctgcaattac aggcataagc cactgtgcct     300
ggccctatcc cttttaattt tctaagtgac cagtaataaa caatgatttg tttattacta     360
ggtagcagga gaaaaaattt ttagtcactt ttccagctaa gaatttcatt taaagatacc     420
tatgacatat cttgtggtac taagaatatt agagaactgg aaatccagtt tttttgtggt     480
tttttaagaa agagaatctg actccattgc ccagcttgga gagcagtggt gcaatagctg     540
gggctacagg cgtgagccac cacaccaggc ctggaaaccc agttttaatt tgtgaactac     600
aaatggttgg caactgattc cttaattgtt attgcaggag taggcccaac atgagtccat     660
atgtagccct tctctg                                                    676

<210> SEQ ID NO 2
<211> LENGTH: 544
<212> TYPE: DNA
<213> ORGANISM: Homo sapiens

<400> SEQUENCE: 2
agggttgagg ctgggaacag ggagaacttc aaatgggcac aagaactcgt ttcggcatga      60
tagaaatgtt ccaaaatgat actatggtaa tggtttcaca attcaaattt gctaaaactt     120
actgagttgt gtacttaact gaatttttata gtatgagaat tatatctcaa taaagctgta     180
aacaaataaa ataactctat agaccttact gaaatagatg tcagttgcaa ggcatcatct     240
cccatttcct gtgcaattct atctcctttta catttgaaag gcttgagtca caccagccag     300
ctggtggtct ttgatccccg ctctgggtcc cttaccctaa agaaaggact tgagcacttt     360

```
ctaagggtaa actctctgga gacttttca gaaaggtctc aacaagggtc cacttattct    420
cggggaagct cataaaagaa acattattgg tctcttgaaa gttcaaaagg gccattttat    480
gagatgagaa tgaatgactt ccattctt cttgctttc attgtagaag tgacttacat      540
taag                                                                  544
```

<210> SEQ ID NO 3
<211> LENGTH: 432
<212> TYPE: DNA
<213> ORGANISM: Homo sapiens

<400> SEQUENCE: 3

```
gggtaggata tggctatgtg actttctaag ctatagctat ggaaaacatt gaaacaaaat     60
tcacgcatgc cgtgtactgt gcccagaaat tgtagacttg tctgggtggt gttaaggatt    120
tgacctattg agagtactca cacctgcttc ttacattcaa gttgttaatc cttcgttcag    180
aaaaggagac atattaggaa atatgtgaat ggactgctgt gacttaaatc ttaagtgttt    240
aggctcttaa actggttcaa actaaaataa cattgatgaa atagtgtttt agacttctgt    300
tacatttatt atatttcaga aacctgtgtg agttgactt actctcattt aagatctagg     360
actttgttgg aacgcttgcc tgagttctaa gttgtaacaa agggtcctga aaatatttag    420
ttacccaaaa tt                                                        432
```

<210> SEQ ID NO 4
<211> LENGTH: 493
<212> TYPE: DNA
<213> ORGANISM: Homo sapiens

<400> SEQUENCE: 4

```
atgaactcgg tttaagacag ggcttcttca ccattgcgag aacgttcacc gggacgagtg     60
gcaagagtct tggcttggat agcatgaaga gccccagtac aaggaagaat actggaaatg    120
ctcaattcgt ggagcgcgtt taaacgacga tttatttggt tttcaatgat cgaggactta    180
tgacaggatg attacatttg accttgggac atgaacgctt ggactgctga cttgtgtgta    240
aagctgtttt gcttgtttgt gtcttgcttg acagtggttc tcgatcatga tgatacctga    300
tgctttggac atgtccactt actcctctat tattcgttgg atcattgttt attctgatag    360
atagtgactt atgttcggat gtcgatcaca ggattgtgat tgttagtcca ctgtatctct    420
gatcgaatag gtctatatat tattatttag atagaaaaag tagcaatcca cttaggagat    480
ttattgatct gct                                                        493
```

<210> SEQ ID NO 5
<211> LENGTH: 418
<212> TYPE: DNA
<213> ORGANISM: Homo sapiens

<400> SEQUENCE: 5

```
ctattcctat ctaatgctag tcttcccact tgggcacttg attcccctct tgcatactca     60
agggcttggc ttctatagct accccttca tttgcatcgt tagttttttc acttgcaata     120
atttactatc agccctcttg gccaggtgca gtggctcacc cgtcatccca gcactttggg    180
aggccaaagt gggtggatca cttgaggtcg gaagttcgag accagcctgg ccaacatggc    240
aaaaccctgt ctctactaaa agtacaaaaa ttagccagga atggtagcac atgcctgtaa    300
tcccagctac tcgggaggct gaggcagaat cgcttgagcc caggaggcgg aggttgcagt    360
```

-continued

```
gagccaagat ggcaccactg cactccagcc tgggcaacag agcaagaaga ctccatct      418

<210> SEQ ID NO 6
<211> LENGTH: 1063
<212> TYPE: DNA
<213> ORGANISM: Homo sapeins

<400> SEQUENCE: 6
ccaattttcc ccttttggaa tgggaatgtt tacccaatgt ctataccccc attgtatctt       60
gggagtaaat aagttattac agggtcatag gtggaaggaa ctcatcttct tcagataaga     120
ttttggactt tggagttaat gttgaaataa gttaagactt tagggactg ttaagaagag      180 attattgtat tttgtgatgt gagaaagaca ggagatttaa gggggccaga ggcagaagga     240
aatagtttgt atatttgtcc ctgcccaaat ttcacattga aatgtaatcc ccaatgttgg     300
tggtagggcc tagtgggaag tgtttgtctg atggtggcag atccatgatg aatgacttgg     360
taccattaat ttggtgatga gttgtctttc tcacttcaca tatccagttg tttaaaagtg     420
tggggtccct cccccaacc cctgccttgc tcctgctttc acaatgtgaa gcgcctgctc       480
ccacttcact ttccgccatg agtaaaagct ccttgaggcc ttcccagaag ctaagcagat     540
gccagagcac catgcttcct gtacaacctg cagaatcatg agccaattaa aactcttttc     600
tttataaatt acccagtctc agatatttct ttatagcaag aatggcctac tacacaaaat     660
tggtattgta tgaactgtac tccggttgga gtaaatttgt ttttgacaca agcgtaggtt     720
agtagctctg aagctatatt aaatgtatac tagagttgaa caaataataa attgtagata     780
atgagagcca gattacaaga aagaagtgac aggtaagcca gggggaagg ctagaatgaa      840 ctgtgtggca cgggattagt gttcgcaata tcacaagaat gcacatttat gcaatacaga    900
aatagagata tgtgagtata catggtgaag tatacataca tatatgaggg gacctaggag    960
caatgatacc ttgggagcaa tgaacacacc taaagcccag atcttggttt ctaaatacta   1020
ttctccaata aaagagtcta aggtctttaa agaaatggtt tat                     1063
```

POLYNUCLEOTIDES RELATED TO PANCREATIC DISEASE

CROSS-REFERENCE TO RELATED APPLICATIONS

This application claims the benefit of prior U.S. Provisional Application Serial No. 60/118,302, filed Feb. 2, 1999, now abandoned, which application is incorporated herein by reference.

TECHNICAL FIELD OF THE INVENTION

This invention relates to genes differentially expressed in pancreatic disease, in particular, pancreatic cancer, dysplasis, and diabetes. More specifically, it relates to polynucleotides that are differentially regulated in pancreatic cancer and dysplasia.

BACKGROUND OF THE INVENTION

Cancer of the pancreas is the fifth leading cause of cancer death in the United States. According to the American Cancer Society, approximately 28,000 people will die of pancreatic cancer in the United States in 1998. The pancreas is a tongue-shaped glandular organ composed of both endocrine and exocrine gland portions, as well as ducts that connect the pancreas to the bile duct and small intestine. The endocrine portion of the pancreas secretes hormones, such as insulin and glucagon which are involved in blood sugar regulation, into the bloodstream. The exocrine portion of the pancreas produces pancreatic enzymes involved in the digestion of fats and proteins; these enzymes are delivered to the bile duct and into the small intestine.

Little is known about the causes of pancreatic cancer, although it is apparent that a high risk of developing pancreatic cancer, without a corresponding increase in the risk of developing other cancers, may be passed along in some families. Cigarette smoking is the most consistently observed non-genetic risk factor for tumor development, with the disease being two to three times more common in heavy smokers than in nonsmokers. However, it is uncertain whether this apparent association reflects a direct carcinogenic effect of metabolites of cigarette smoke or whether an as yet undefined exposure is responsible for the observed enhanced risk. Both chronic pancreatitis and long-standing diabetes mellitus have each been linked to an increased risk of pancreatic cancer. Mutations in K-ras genes have been found in more than 85 percent of specimens of human pancreatic cancer. The development of pancreatic cancer has also been associated with a mutation of the $p16^{INK4}$ gene located on chromosome 9p21, a gene which is also implicated in the pathogenesis of cutaneous malignant melanoma.

Overall, pancreatic cancers occur twice as frequently in the pancreatic head (about 70% of cases) as in the body (about 20%) or tail (about 10%). Pancreatic adenocarcinomas usually begin in the ducts of the pancreas, but may sometimes develop from the acinar cells. Greater than 90% of pancreatic cancers are ductal adenocarcinomas, with the remaining 5 to 10% being islet cell tumors. Cancers of the exocrine cells of the pancreas are usually adenocarcinomas (about 95%). Less common cancers of the exocrine pancreas include adenosquamous carcinomas, squamous cell carcinomas, and giant cell carcinomas.

The initial symptoms of pancreatic cancer are usually nonspecific (e.g., abdominal pain and weight loss) and are frequently disregarded. The deep anatomic location of the pancreas makes detection of small localized tumors unlikely during the routine abdominal examination. Even in patients with confirmed pancreatic cancer, an abdominal mass is palpable in only 15–25% of cases. Diagnosis of pancreatic cancer is further complicated by the occurrence of dysplastic cells, i.e., abnormal cells that are not cancerous. Thus., even a biopsy can result in an erroneous diagnosis. Biopsy diagnoses may also be complicated by other underlying pancreatic disorders such as diabetes or pancreatitis. Unfortunately, because pancreatic cancer is generally very aggressive, some 80–90% of patients have regional and distant metastases by the time they are diagnosed and only 3% of the 24,000 patients annually diagnosed with pancreatic cancer live more than 5 years after diagnosis.

Although early and accurate diagnosis can thus be extremely important in treatment success, there are presently no reliable screening tests for detecting pancreatic cancer in asymptomatic persons. Imaging procedures such as magnetic resonance imaging and computed tomography are too costly to use as routine screening tests, while more accurate tests such as endoscopic retrograde cholangiopancreatography (ERCP) and endoscopic ultrasound are inappropriate for screening asymptomatic patients due to their invasiveness. Abdominal ultrasonography is a noninvasive screening test, but there is little information on the efficacy of abdominal ultrasound as a screening test for pancreatic cancer in asymptomatic persons. In symptomatic patients with suspected disease it has a reported sensitivity of 40–98% and a specificity as high as 90–94%. Conventional ultrasonography is limited by visualization difficulties in the presence of bowel gas or obesity and by its range of resolution (2–3 cm). Even tumors less than 2 cm in diameter are frequently associated with metastatic disease, thus limiting the ability of ultrasound to detect early disease.

Most persons with pancreatic malignancy have elevated levels of certain serologic markers such as CA19-9, peanut agglutinin, pancreatic oncofetal antigen, DU-PAN-2, carcinoembryonic antigen, alpha-fetoprotein, CA-50, SPan-1, and tissue polypeptide antigen (Rhodes et al. (1990) *Bailleres Clin. Gastroenterol.* 4:833; Steinberg (1990) *Am. J. Gastroenterol.* 85:350; Satake et al. (1990) *Int. J. Pancreatol.* 7:25; Satake (1991) *Int. J. Pancreatol.* 9:93). None of these markers is, however, tumor specific or organ specific (Satake (1991), supra). Elevations of various serologic markers also occur in significant proportions of persons with benign gastrointestinal diseases or malignancies other than pancreatic cancer (Carter (1990) *Gut* 31:494; Rhodes et al. (1990), supra; Satake et al. (1990), supra; Satake (1991), supra). Most of these markers have been studied exclusively in high-risk populations, such as symptomatic patients with suspected pancreatic cancer. CA19-9 has probably achieved the widest acceptance as a serodiagnostic test for pancreatic carcinoma in symptomatic patients, with an overall sensitivity of approximately 80% (68–93%) and specificity of 90% (73–100%); sensitivity was highest in patients with more advanced disease (Steinberg (1990), supra; Satake et al. (1990), supra). Among healthy subjects, CA19-9 has good specificity (94–99%) (DelVillano et al. (1983) *Clin. Chem.* 29:549; Ritts et al. (1984) *Int. J. Cancer* 33:339; Fabris et al. (1988) *Am. J. Gastroenterol.* 83:549) but nevertheless generates a large proportion of false-positive results due to the very low prevalence of pancreatic cancer in the general population (Frebourg et al. (1988) *Cancer* 62:2287; Homma et al. (1991) *Int. J. Pancreatol.* 9:119). The predictive value of a positive test could be improved if a population at substantially higher risk could be identified. Diabetes mellitus in older adult patients might be useful as a marker for a population at high risk of having pancreatic cancer. Cohort studies have reported incidences of pancreatic cancer among diabetic patients ranging from 51 to 166/100,000 person-years (Everhart et al. (19950 JAMA 273:1605).

The inadequacies of conventional diagnostic methods for pancreatic cancer highlight the need for diagnostic and therapeutic methods and compositions, as well as for a better understanding of the disease to provide the basis for more rationale and more quickly responsive therapy. The fact that some patients suffer from combinations of pancreatic cancer, dysplasia, and/or diabetes further complicates diagnosis and rationale therapy design. The present invention addresses this need by providing nucleotide sequence that are differentially expressed in these diseases.

Relevant Literature

A review of diagnostic methods available for pancreatic cancer is provided in Bramhall (1998) *Int. J. Pancreatol.* 23:83; Friess et al. (1997) *Digestion* 58:557; and Lemoine (1997) *Digestion* 58:550; as well as at the National Cancer Institute web site http://cancernet.nci.nih.gov/clinpdq/soa/Pancreatic_cancer_Physician.html.

Expression analysis using nucleic acid arrays is reviewed by Ramsay (1998) *Nat. Biotech.* 16:40–44. Methods for creating microarrays of biological samples, such as arrays of DNA samples to be used in DNA hybridization assays, are described in PCT publication no. WO 95/35505, published Dec. 28, 1995; U.S. Pat. No. 5,445,934; Drmanac et al., Science 260:1649; and Yershov et al. (1996) *Genetics* 93:4913.

Quantitative monitoring of gene expression patterns with a complementary DNA microarray is described in Schena et al. (1995) *Science* 270:467. DeRisi et al. (1997) *Science* 270:680–686 explore gene expression on a genomic scale. Analysis of gene expression patterns in human cancer using a cDNA microarray is described in DeRisi et al. (1996) *Nat. Genet.* 14:457.

Use of differential display to identify differential gene expression is described in, for example, U.S. Pat. Nos. 5,776,683; and 5,807,680.

Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

SUMMARY OF THE INVENTION

The present invention is based on the discovery of polynucleotides that represent novel genes that are differentially expressed in pancreatic disease, e.g., pancreatic cancer, dysplasia, pancreatitis, or diabetes. The invention features methods of identifying cells affected by such pancreatic diseases by detection of a gene product encoded by such differentially expressed genes, as well as methods of modulating expression of such gene products to effect therapy (e.g., to decrease growth and/or affect abnormal characteristics of cancerous or dysplastic pancreatic cells.)

Accordingly, in one aspect the invention features a library of differentially expressed genes, where the library includes the sequence information of at least one of the polynucleotides of SEQ ID NOS:1–6. The library may be provided as a nucleic acid array or in a computer-readable format, and may include relative amounts of the polynucleotides of SEQ ID NOS:1–6, where the relative amounts are representative of relative amounts of the polynucleotides found in a diseased pancreatic cell.

The invention also features an isolated polynucleotide having a sequence of at least 90% sequence identity to an identifying sequence of SEQ ID NOS:1–6 or degenerate variants thereof. In related aspects, the invention features arrays and recombinant host cells having a polynucleotide of the invention. In one embodiment the polynucleotide includes the nucleotide sequence of an insert contained in one of the clones HX2134-4, HX2144-1, HX2145-3, HX2162-3, HX2166-6, or HX2192-1, which have been deposited as ATCC accession number 98896.

In another aspect the invention features an isolated polypeptide encoded by a differentially express gene of the invention, as well as antibodies that specifically bind such polypeptides.

The invention also features a method of identifying a cancerous pancreatic cell, where the method involves detecting at least one differentially expressed gene product, where the gene product is encoded by a gene having a sequence of SEQ ID NOS:1–6 in a test sample, where the test sample is derived from a test cell suspected of being a cancerous pancreatic cell, and comparing an amount of the detected differentially expressed gene product with an amount of the differentially expressed gene product in a control sample, where the control sample is derived from a cancerous pancreatic cell. Detection of an amount of the differentially expressed gene product in the test sample that is similar to an amount of the gene product in the control sample indicates that the test cells is a cancerous pancreatic cell. In one embodiment, detection is accomplished by hybridization of the test sample to a reference array, wherein the reference array comprises an identifying sequence of at least one of SEQ ID NOS:1–6.

In another aspect, the invention features therapeutic compositions having an active agent for modulation of expression of a gene differentially expressed in cancerous or dysplastic pancreatic cells. In specific embodiments, the active agent of the therapeutic composition effects a decrease in biological activity of a gene product encoded by a gene having a sequence of SEQ ID NO:2, effects an increase in biological activity of a gene product encoded by a gene having a sequence of SEQ ID NO:6, effects an increase in biological activity of a gene product encoded by a gene having a sequence of SEQ ID NOS:1 or 3, or effects a decrease in biological activity of a gene product encoded by a gene having a sequence of SEQ ID NOS:4 or 5.

A primary object of the invention is to provide differentially expressed polynucleotides and fragments thereof that are useful in diagnosis of pancreatic disease, as well as in rational drug and therapy design.

These and other objects of the invention are provided by one or more of the embodiments described below.

DETAILED DESCRIPTION OF THE PREFERRED EMBODIMENTS

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Definitions

The term "differentially expressed gene" is intended to encompass a polynucleotide that may include an open reading frame encoding a gene product (e.g., a polypeptide), as well as introns of such genes and adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome. In general, a difference in expression level associated with a decrease in expression level of at least about 25%, usually at least about 50% to 75%, more usually at least about 90% or more is indicative of a differentially expressed gene of interest, i.e., a gene that is underexpressed or down-regulated in the test sample relative to a control sample. Furthermore, a difference in expression level associated with an increase in expression of at least about 25%, usually at least about 50% to 75%, more usually at least about 90% and may be at least about 1½-fold, usually at least about 2-fold to about 10-fold, and may be about 100-fold to about 1,000-fold increase relative to a control sample is indicative of a differentially expressed gene of interest, i.e., an over-expressed or up-regulated gene.

"Differentially expressed polynucleotide" as used herein means a nucleic acid molecule (RNA or DNA) having a sequence that represents a differentially expressed gene, e.g., the differentially expressed polynucleotide comprises a sequence (e.g., an open reading frame encoding a gene product) that uniquely identifies a differentially expressed gene so that detection of the differentially expressed polynucleotide in a sample is correlated with the presence of a differentially expressed gene in a sample. "Differentially expressed polynucleotides" is also meant to encompass fragments of the disclosed polynucleotides, e.g., fragments retaining biological activity, as well as nucleic acids that are homologous, substantially similar, or substantially identical (e.g., having about 90% sequence identity) to the disclosed polynucleotides.

"Reference sequences" or "reference polynucleotides" as used herein in the context of differential gene expressive analysis and diagnosis refers to a selected set of polynucleotides, which selected set includes at least one or more of the differentially expressed polynucleotides described herein. A plurality of reference sequences, preferably comprising positive and negative control sequences, may be included as reference sequences. Additional reference sequences that may be used as reference sequences are found in Genbank, Unigene, and other nucleotide sequence databases (including, e.g., expressed sequence tag (EST), partial, and full-length sequences).

"Reference array" means an array having reference sequences for use in hybridization with a sample, where the reference sequences include all, at least one of, or any subset of the differentially expressed polynucleotides listed in Table 1. Usually such an array will include at least 3 different reference sequences, and may include any one or all of the provided differentially expressed sequences. Arrays of interest may further comprise sequences, including polymorphisms, of other genetic sequences, particularly other sequences of interest for screening for a pancreatic disorder (e.g., pancreatic cancer, pancreatic dysplasia, pancreatitis, diabetes syndromes, and the like). The oligonucleotide sequence on the array will usually be at least about 12 nt in length, and may be of about the length of the sequences provided in Table 1, or may extend into the flanking regions to generate fragments of 100 nt to 200 nt in length or more.

A "reference expression pattern" or "REP" as used herein refers to the relative levels of expression of a selected set of genes, particularly of differentially expressed genes, that is associated with a selected cell type, e.g., a normal cell (e.g., normal pancreatic cell), a cancerous cell, a cell exposed to an environmental stimulus, and the like.

A "test expression pattern" or "TEP" refers to relative levels of expression of a selected set of genes, particularly of differentially expressed genes, in a cell of a test sample (e.g., a cell of unknown or suspected disease state, from which mRNA is isolated).

"Diagnosis" as used herein generally includes determination of a subject's susceptibility to a disease or disorder, determination as to whether a subject is presently affected by a disease or disorder, as well as to the prognosis of a subject affected by a disease or disorder. The present invention encompasses diagnosis of subjects in the context of pancreatic cancer (e.g., ductal adenocarcinoma or other pancreatic cancer, as well as any stage of such cancers (e.g., stages I to IV in severity), pancreatic dysplasia, pancreatitis, and diabetes (e.g., Type I or Type II diabetes).

"Pancreatic cancer" is meant to encompass benign or malignant forms of pancreatic cancer, as well as any particular type of cancer arising from cells of the pancreas (e.g., duct cell carcinoma, acinar cell carcinoma, papillary carcinoma, adenosquamous carcinoma, undifferentiated carcinoma, mucinous carcinoma, giant cell carcinoma, mixed type pancreatic cancer, small cell carcinoma, cystadenocarcinoma, unclassified pancreatic cancers, pancreatoblastoma, and papillary-cystic neoplasm, and the like.

"Pancreatitis" as used herein is meant to encompass chronic pancreatitis, acute pancreatitis, and pancreatic abscesses associated with pancreatic inflammation.

"Subjects" or "patients" as used herein is meant to encompass any subject or patient amenable to application of the diagnostic and/or therapeutic methods of the invention. Mammalian subjects and patients, particularly human subjects or patients are of particular interest.

"Sample" or "biological sample" are generally used to refer to samples of biological fluids or tissues, particularly samples obtained from pancreatic tissues, especially from pancreatic cells of the type associated with the disease for which the diagnostic application is designed (e.g., ductal adenocarcinoma), and the like. "Samples" is also meant to encompass derivatives and fractions of such samples (e.g., cell lysates). Where the sample is solid tissue, the cells of the tissue may be dissociated or tissue sections may be analyzed.

Overview of the Invention

In general, the invention is based on the discovery of polynucleotides that represent genes that are differentially expressed in pancreatic cells associated with pancreatic disease, particularly pancreatic cancer, dysplasia, pancreatitis, and/or diabetes. Differential expression of genes in pancreatic cells affected with cancer is determined by, for example, detecting genes expressed in a cancerous pancreatic cell, and comparing the level of gene expression to expression of those same genes in a normal pancreatic cell (i.e., a pancreatic cell that is not affected by a pancreatic cancer) and/or a dysplastic pancreatic cell.

The differentially expressed polynucleotides described herein were identified using differential displays of samples from normal pancreatic cells, dysplastic pancreatic cells, cancerous pancreatic cells, pancreatic cells from a subject affected by pancreatitis, and pancreatic cells from a subject affected by diabetes (Type I or Type II). The sequence of specific polynucleotides that represent differentially expressed genes of the present invention are shown in SEQ ID NOS:1–6. Differential expression of the genes represented by these polynucleotides was observed to be as follows:

1. SEQ ID NOS:1 and 3 are expressed at a relatively lower level (i. e., down-regulated) in a dysplastic pancreatic cell;
2. SEQ ID NO:2 is expressed at a relatively higher level (i.e., up-regulated) in a cancerous pancreatic cell;
3. SEQ ID NOS:4 and 5 are expressed at a relatively higher level in a dysplastic pancreatic cell; and
4. SEQ ID NO:6 is expressed at a relatively lower level in both pancreatic cells affected by dysplasia and cancerous pancreatic cells.

The invention will now be described in further detail.

Nucleic Acid Compositions

The invention features polynucleotides that are differentially expressed in pancreatic disease (e.g., cancer, dysplasia, diabetes, or pancreatitis). Novel nucleic acid compositions of the invention of particular interest comprise a sequence set forth in any one of SEQ ID NOS:1–6 or an identifying sequence thereof. An "identifying sequence" is a contiguous sequence of residues at least about 10 nt to about 20 nt in length, usually at least about 50 nt to about 100 nt in length, that uniquely identifies a polynucleotide sequence, e.g., exhibits less than 90%, usually less than about 80% to about 85% sequence identity to any contiguous nucleotide sequence of more than about 20 nt. Thus, the subject novel nucleic acid compositions include full length cDNAs or mRNAs that include an identifying sequence of contiguous nucleotides from any one of SEQ ID NOS:1–6, as described above.

The polynucleotides of the invention also include naturally occurring variants of the nucleotide sequences (e.g., degenerate variants, allelic variants, etc.). Allelic variants of the polynucleotides of the invention are identified by hybridization of putative allelic variants with nucleotide sequences disclosed herein under stringent conditions. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided polynucleotide sequences, e.g. allelic variants, genetically altered versions of the gene, etc., generally bind to the provided polynucleotide sequences (SEQ ID NOS:1–6) under stringent hybridization conditions. In general, allelic variants contain 15–25% base pair mismatches, and may contain as little as even 5–15%, or 2–5%, or 1–2% base pair mismatches, as well as a single base-pair mismatch.

The invention also encompasses homologs corresponding to the polynucleotides of SEQ ID NOS:1–6, where the source of homologous genes may be any mammalian species, e.g., primate species, particularly human; rodents, such as rats, canines, felines, bovines, ovines, equines, yeast, nematodes, etc. Between mammalian species, e.g., human and mouse, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10. In general, variants of the invention have a sequence identity greater than at least about 65%, preferably at least about 75%, more preferably at least about 85%, and may be greater than at least about 90% or more as determined by the Smith-Waterman homology search algorithm as implemented in MPSRCH program (Oxford Molecular) using an affine gap search with the following search parameters: gap open penalty: 12; and gap extension penalty: 1. The sequences provided herein are essential for recognizing related and homologous polynucleotides in database searches.

The subject nucleic acids may be cDNAs or genomic DNAs, as well as fragments thereof, particularly fragments that encode a biologically active gene product and/or are useful in the methods disclosed herein (e.g., in diagnosis, as a unique identifier of a differentially expressed gene of interest, etc.). The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' and 3' end of the transcribed region. The genomic DNA may be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue, stage-specific, or disease-state specific expression.

The nucleic acid compositions of the subject invention may encode all or a part of the subject differentially expressed polypeptides. Double or single stranded fragments may be obtained from the DNA sequence by chemically synthesizing oligonucleotides in accordance with conventional methods, by restriction enzyme digestion, by PCR amplification, etc. Isolated polynucleotides and polynucleotide fragments of the invention comprise at least 10, 11, 12, 15, 18, 20, 25, 30, 35, 40, 45, 50, 60, 70, 74, 80, 90, 100, 125, 150, 154, 175, 200, 250, 300, or 350 contiguous nucleotides selected from the polynucleotide sequences as shown in SEQ ID NOS:1–6. For the most part, fragments will be of at least 15 nt, usually at least 18 nt or 25 nt, and may be at least about 50 contiguous nt in length. In a preferred embodiment, the polynucleotide molecules comprise a contiguous sequence of at least twelve nucleotides selected from the group consisting of the polynucleotides shown in SEQ ID NOS:1–6.

Probes specific to the polynucleotides of the invention may be generated using the polynucleotide sequences disclosed in SEQ ID NOS:1–6. The probes are preferably at least a 12, 14, 16, 18, 20, 22, 24, or 25 nucleotide fragment of a corresponding contiguous sequence of SEQ ID NOS:1–6, and can be less than 2, 1, 0.5, 0.1, or 0.05 kb in length. The probes can be synthesized chemically or can be generated from longer polynucleotides using restriction enzymes. The probes can be labeled, for example, with a radioactive, biotinylated, or fluorescent tag.

The differentially expressed polynucleotides of the subject invention are isolated and obtained in substantial purity, generally as other than an intact chromosome. Usually, the DNA will be obtained substantially free of other naturally-occurring nucleic acid sequences, generally being at least about 50%, usually at least about 90% pure and are typically "recombinant", e.g., flanked by one or more nucleotides with which it is not normally associated on a naturally occurring chromosome.

The polynucleotides of the invention can be provided as linear or within a circular molecules. They can be on autonomously replicating molecules (vectors) or on molecules without replication sequences. They can be regulated by their own or by other regulatory sequences, as is known in the art. The polynucleotides of the invention can be introduced into suitable host cells using a variety of techniques which are available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

The subject nucleic acid compositions can be used to, for example, produce polypeptides, as probes for the detection of mRNA of the invention in samples or extracts of human cells, to generate additional copies of the polynucleotides, to generate ribozymes or antisense oligonucleotides, and as single stranded DNA probes or as triple-strand forming oligonucleotides. The probes described herein can be used to, for example, determine the presence or absence of the polynucleotide sequences as shown in SEQ ID NOS:1–6 or variants thereof in a sample.

Polypeptide Compositions

The subject invention also provides polypeptides encoded by a differentially expressed polynucleotide of the invention, e.g, a polypeptide encoded by a polynucleotide having a sequence of any of SEQ ID NOS:1–6. The term "polypeptide" composition as used herein refers to both the full length polypeptide encoded by the recited polynucleotide, the polypeptide encoded by the gene represented by the recited polynucleotide, as well as portions or fragments thereof. "Polypeptides" also includes variants of the naturally occurring proteins, where such variants are homologous or substantially similar to the naturally occurring protein, and can be of an origin of the same or different species as the naturally occurring protein (e.g., human, murine, or some other species that naturally expresses the recited polypeptide, usually a mammalian species). In general, variant polypeptides have a sequence that has at least about 80%, usually at least about 90%, and more usually at least about 98% sequence identity with a differentially expressed polypeptide of the invention, as measured by BLAST using the parameters described above. The variant polypeptides may be naturally or non-naturally glycosylated, i.e., the polypeptide has a glycosylation pattern that differs from the glycosylation pattern found in the corresponding naturally occurring protein.

The invention also encompasses homologs of the disclosed polypeptides (or fragments thereof) where the homologs are isolated from other species, i.e. other animal or plant species, where such homologs, usually mammalian species, e.g. rodents, such as mice, rats; domestic animals, e.g., horse, cow, dog, cat; and humans. By homolog is meant a polypeptide having at least about 35%, usually at least about 40% and more usually at least about 60% amino acid sequence identity a particular differentially expressed protein as identified above, where sequence identity is determined using the BLAST algorithm, with the parameters described supra.

In general, the polypeptides of the subject invention are provided in a non-naturally occurring environment, e.g. are separated from their naturally occurring environment. In certain embodiments, the subject protein is present in a composition that is enriched for the protein as compared to a control. As such, purified polypeptide is provided, where by purified is meant that the protein is present in a composition that is substantially free of non-differentially expressed polypeptides, where by substantially free is meant that less than 90%, usually less than 60% and more usually less than 50% of the composition is made up of non-differentially expressed polypeptides.

In certain embodiments of interest, the subject protein is present in a composition that is substantially free of the constituents that are present in its naturally occurring environment. For example, a composition comprising a protein according to the subject invention in this embodiment will be substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the protein's natural environment constituents will still be present in the composition prepared from the naturally occurring source.

The proteins of the subject invention may also be present as an isolate, by which is meant that the protein is substantially free of both non-differentially expressed polypeptides and other naturally occurring biologic molecules, such as oligosaccharides, polynucleotides and fragments thereof, and the like, where substantially free in this instance means that less than 70%, usually less than 60% and more usually less than 50% of the composition containing the isolated polypeptide is a non-differentially expressed, naturally occurring biological molecule. In certain embodiments, the protein is present in substantially pure form, where by substantially pure form is meant at least 95%, usually at least 97% and more usually at least 99% pure.

In addition to the naturally occurring proteins, polypeptides that vary from the naturally occurring differentially expressed polypeptides are also provided. By differentially expressed polypeptides is meant polypeptides having an amino acid sequence encoded by an open reading frame (ORF) of a differentially expressed gene, especially a differentially expressed polynucleotide of the invention, polynucleotide, including the full length polypeptide and fragments thereof, particularly biologically active fragments and/or fragments corresponding to functional domains; and including fusions of the subject polypeptides to other proteins or parts thereof. Fragments of interest will typically be at least about 10 aa to at least about 15 aa in length, usually at least about 50 aa in length, and may be as long as 300 aa in length or longer, but will usually not exceed about 1000 aa in length, where the fragment will have a stretch of amino acids that is identical to a differentially expressed polypeptide encoded by a differentially expressed gene having a sequence of any of SEQ ID NOS:1–6, or a homolog thereof.

Fusion polypeptides encompassed by the present invention are composed of at least two protein segments. The first protein segment consists of at least six, eight, ten, twelve, fifteen, twenty or thirty contiguous amino acids of a polypeptide sequence expressed from a polynucleotide sequence as shown in SEQ ID NOS:1–6. The first protein segment is fused to a second protein segment by means of a peptide bond. The second protein segment can be a full-length protein or a fragment of a protein of the same, similar, or different origin. The second protein or protein fragment can be labeled with a detectable marker, such as a radioactive or fluorescent tag, or an enzyme that can generate a detectable product upon contact with a substrate (e.g., β-galactosidase). A fusion protein can be used, for example, to facilitate delivery to a particular location in a cell or tissue, in various biochemical or immunological assays, such as the yeast two-hybrid technique, or as an immunogen. Techniques for making fusion proteins, either recombinantly or by covalently linking two protein segments, are well know in the art.

Preparation of Differentially Expressed Polypeptides

The subject polypeptides may be obtained from naturally occurring sources, but are preferably synthetically produced. Where obtained from naturally occurring sources, the source chosen will generally be a pancreatic cell. The subject polypeptide compositions may be synthetically derived by expressing a recombinant gene encoding the polypeptide of interest in a suitable host. In general, an expression cassette in an expression vector is used for recombinant expression. The expression vector provides transcriptional and translational initiation regions, for inducible or constitutive expression of an operably linked coding region, and transcriptional and translational termination regions. These control regions may be native to a selected differentially expressed gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The polypeptides may be expressed in prokaryotes or eukaryotes in accordance with conventional ways, depending upon the purpose for expression. For large scale production of the encoded protein, a unicellular organism, such as *E. coli, B. subtilis, S. cerevisiae*, insect cells in combination with baculovirus vectors, or cells of a higher organism such as vertebrates, particularly mammals, e.g., COS 7 cells, may be used as the expression host cells. In some situations, it is desirable to express the differentially expressed polynucleotide in eukaryotic cells, where the encoded polypeptide will benefit from native folding and post-translational modifications. Small peptides can also be synthesized in the laboratory. Polypeptides that are encoded by subsets of the complete differentially expressed sequence may be used to identify and investigate parts of the polypeptide important for function.

Where it is desirable to produce a polypeptide of the invention in a yeast host cell, suitable expression systems in yeast may be selected from those described in Hinnen et al., *Proc. Natl. Acad. Sci. USA* (1978) 75: 1929; Ito et al., *J. Bacteriol.* (1983) 153:163; Kurtz et al., *Mol. Cell Biol.* (1986) 6: 142; Kunze et al.,*J. Basic Microbiol.* (1985) 25:14 1; Gleeson et al., *J. Gen. Microbiol.* (1986) 132: 3459; Roggenkamp, et al., *Mol. Gen. Genet.* (1986) 202:302; Das et al.,*J. Bacteriol.* (1984) 158: 1165; De Louvencourt et al., *J. Bacteriol.* (1983) 154: 737; Van den Berg et al., *BioTechnology* (1990) 8: 135; Kunze et al., *J. Basic Microbiol.* (1985) 25:141; Cregg et al., *Mol. Cell. Biol.* (1985) 5:3376; U.S. Pat. Nos. 4,837,148; 4,929,555; Beach and Nurse, *Nature* (1981) 300:706; Davidow et al., *Curr. Genet.* (1985) 10: 3 80; Gaillardin et al., *Curr. Genet.* (1985) 10: 49; Ballance et al., *Biochem. Biophys. Res. Commun.* (1983) 112: 284–289; Tilbum et al., *Gene* (1983) 26:205–22 1; Yelton et al., *Proc. Natl. Acad. Sci. USA* (1984) 81:1470–1474; Kelly and Hynes, *EMBO J.* (1985) 4:475479; EP 244,234; and WO 91/00357.

Expression of the polynucleotides of the invention in insects can be accomplished as described in U.S. Pat. No. 4,745,051, Friesen et al. (1986) "The Regulation of Baculovirus Gene Expression" in: *The Molecular Biology of Baculovirus* (W. Doerfler, ed.); EP 127,839; EP 155,476; Vlak et al., *J. Gen. Virol.* (1988) 69: 765–776; Miller et al., *Ann. Rev. Microbiol.* (1988) 42: 177; Carbonell et al., *Gene* (1988) 73: 409; Maeda et al., *Nature* (1985) 315:592–594; Lebacq-Verheyden et al., *Mol. Cell. Biol.* 8: 3129; Smith et al., *Proc. Natl. Acad. Sci. USA* (1985) 82:8404; Miyajima et al., *Gene* (1987) 58: 273; and Martin et al., *DNA* (1988) 7:99. Numerous baculoviral strains and variants and corresponding permissive insect host cells from hosts are described in Luckow et al., *BioTechnol.* (1988) 6: 47–55; Miller et al., in *Genetic Engineering* (Setlow, J. K. et al. eds.), Vol. 8 (Plenum Publishing, 1986), pp. 277–279; and Maeda et al., *Nature,* (1985) 315:592–594.

Mammalian expression of the polynucleotides of the invention can be accomplished as described in Dijkema et al., *EMBO* 1 (1985) 4:76; Gorman et al., *Proc. Natl. Acad. Sci. USA* (1982) 79:6777; Boshart et al., *Cell* (1985) 41:521; and U.S. Pat. No. 4,399,216. Other features of mammalian expression can be facilitated as described in Ham and Wallace, *Meth. Enzymol.* (1979) 58: 44; Barnes and Sato, *Anal. Biochem.* (1980) 102:255; U.S. Pat. Nos. 4,767,704; 4,657,866; 4,927,762; 4,560,655; WO 90/103430; WO 87/00195; and U.S. Pat. No. RE30,985.

Once the source of the polypeptide is identified and/or prepared, e.g. a transfected host expressing the protein is prepared, the polypeptide is then purified to produce the desired composition. Any convenient protein purification procedures may be employed, where suitable protein purification methodologies are described in Guide to Protein Purification, (Deuthser ed.) (Academic Press, 1990). For example, a lysate may be prepared from the original source, e.g. naturally occurring cells or tissues that express the protein or the expression host expressing the protein, and purified using HPLC, exclusion chromatography, gel electrophoresis, affinity chromatography, and the like.

Antibodies

The present invention also provides antibodies that specifically bind a polypeptide encoded by a differentially expressed polynucleotide or gene of the invention. Suitable antibodies are obtained by immunizing a host animal with a differentially expressed polypeptide. Suitable non-human host animals include mice, rats, sheep, goats, hamsters, rabbits, etc. The origin of the protein immunogen may be mouse, human, rat, monkey etc. The host animal will generally be a different species than from which the immunogen was derived, e.g. human protein used to immunize mice, etc.

The immunogen may comprise the complete protein, or immunogenic fragments and derivatives thereof. Immunogens may include native post-translation modifications, such as glycosylation. Immunogens are produced in a variety of ways known in the art, e.g. expression of cloned genes using conventional recombinant methods, isolation from HEC, etc.

Polyclonal antibodies can be prepared by first immunizing the host animal with a polypeptide, where the polypeptide will preferably be in substantially pure form, comprising less than about 1% contaminant. The protein may be combined with an adjuvant, where suitable adjuvants include alum, dextran, sulfate, large polymeric anions, oil & water emulsions, e.g., Freund's adjuvant, Freund's complete adjuvant, and the like. The protein may also be conjugated to synthetic carrier proteins or synthetic antigens. A variety of hosts may be immunized to produce the polyclonal antibodies (e.g., rabbits, guinea pigs, rodents, e.g. mice, rats, sheep, goats, and the like). The protein is administered to the host, usually intradermally, with an initial dosage followed by one or more, usually at least two, additional boosters. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. The antibody may be purified from the hybridoma cell supernatants or ascites fluid by conventional techniques, e.g. affinity chromatography using, protein A sepharose, etc. Anti-differentially expressed polypeptide antibody may also be produced as a single chain, instead of the normal multimeric structure. Single chain antibodies are described in Jost et al. (1994) *J. Biol. Chem.* 269:26267–73, and others.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. For example, the humanized antibody may be the product of an animal having transgenic human immunoglobulin constant region genes (see for example WO 90/10077 and WO 90/04036). Alternatively, the antibody of interest may be engineered by recombinant DNA techniques to substitute the $CH_1$, $CH_2$, $CH_3$, hinge domains, and/or the framework domain with the corresponding human sequence (see WO 92/02190).

The use of Ig cDNA for construction of chimeric immunoglobulin genes is known in the art (Liu et al. (1987) *Proc. Natl. Acad. Sci. USA* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human constant (C) region genes are readily available from known clones. The choice of isotype will be guided by the desired effector functions, such as complement fixation, or activity in antibody-dependent cellular cytotoxicity. Preferred isotypes are $IgG_1$, $IgG_3$ and $IgG_4$. Either of the human light chain constant regions, kappa or lambda, may be used. The chimeric, humanized antibody is then expressed by conventional methods. Chimeric antibodies may be produced by use of an expression vector (e.g., plasmid, retroviral vector, YAC, EBV-derived episome, etc.), and which may use any promoter, particularly a strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Antibody fragments, such as Fv, $F(ab')_2$ and Fab may be prepared by cleavage of an intact Ig protein, e.g. by protease or chemical cleavage. Alternatively, a truncated gene is designed. For example, a chimeric gene encoding a portion of the $F(ab')_2$ fragment would include DNA sequences encoding the $CH_1$ domain and hinge region of the H chain, followed by a translational stop codon to yield the truncated molecule.

Uses of the Subject Polypeptide and Nucleic Acid Compostions

The compositions of the invention find use in a variety of applications, such as: (a) the identification of differentially expressed gene homologs; (b) as a source of novel promoter elements; (c) the identification of naturally-occurring factors that regulate expression; (d) as probes and primers in hybridization applications, e.g. PCR; (e) the identification of expression patterns in biological specimens; (f) the preparation of cell or animal models for differentially expressed protein function; (g) the preparation of in vitro models for function of differentially expressed polypeptides; etc. Exemplary applications are described below.

Identification of Homologs of Differentially Expressed Polynucleotides

Homologs of the differentially expressed polynucleotide of the invention can be identified by any of a number of methods. For example, a fragment of the provided cDNA may be used as a hybridization probe against a cDNA library from the target organism of interest, where low stringency conditions are used. The probe may be a large fragment, or one or more short degenerate probes. Nucleic acids having a region of substantial identity to the provided differentially expressed nucleic acid sequences, e.g. allelic variants, genetically altered versions of the gene, etc., bind to the sequences of the invention under stringent hybridization conditions. By using probes, particularly labeled probes of DNA sequences, one can isolate homologous or related genes.

Identification of Novel Promoter Elements

The sequence of the 5' flanking region may be utilized for promoter elements, including enhancer binding sites, that provide for regulation in tissues where the subject nucleic acids are expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Identification of Naturally-occurring Factors Regulating Expression

Alternatively, mutations may be introduced into the promoter region to determine the effect of altering expression in experimentally defined systems. Methods for the identification of specific DNA motifs involved in the binding of transcriptional factors are known in the art, e.g., sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232:620–626.

The regulatory sequences may be used to identify cis acting sequences required for transcriptional or translational regulation of nucleic acid expression, especially in different tissues or stages of development, and to identify cis acting sequences and trans-acting factors that regulate or mediate nucleic acid expression. Such transcription or translational control regions may be operably linked to an a polynucleotide of the invention in order to promote expression in cultured cells, or in embryonic, fetal or adult tissues, and for gene therapy.

Probes and Primers

The polynucleotides of the invention can also be used in the design of primers or probes. Small DNA fragments (e.g., less than 100 nt) are useful as probes or primers, as in PCR, hybridization screening, etc. Larger DNA fragments, e.g., greater than 100 nt, are also useful for production of the encoded polypeptide, as described above. For use in amplification reactions, such as PCR, a pair of primers will be used. The exact composition of the primer sequences is not critical to the invention, but for most applications the primers will hybridize to the subject sequence under stringent conditions, particularly under conditions of high stringency, as known in the art. The pair of primers are usually chosen so as to generate an amplification product of at least about 50 nt, more usually at least about 100 nt. Algorithms for the selection of primer sequences are generally known, and are available in commercial software packages.

Identification of Expression Patterns in Biological Specimens

The polynucleotides of the invention may also be used to identify expression of the gene in a biological specimen. Detection of expression of a particular nucleotide sequence in a selected cell is well established in the literature. Briefly, mRNA is isolated from a cell sample. The mRNA may be amplified by RT-PCR, using reverse transcriptase to form a complementary DNA (cDNA) strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to oligonucleotides arrayed on a solid chip may also find use. Detection of mRNA hybridizing to, or amplified by primers specific for, the subject sequence is indicative of expression of a differentially expressed gene in the sample. This particular use of the polynucleotides of the invention is described below in further detail.

Preparation of Mutants

The sequence of a differentially expressed gene, including flanking promoter regions and coding regions, may be mutated in various ways known in the art to generate targeted changes in promoter strength, sequence of the encoded protein, etc. The DNA sequence or protein product of such mutants will usually be substantially similar to the sequences provided herein, e.g., will differ by at least one nucleotide or amino acid, and may differ by at least two, up to ten or more nucleotides or amino acids. The sequence changes may be substitutions (conservative or non-conservative), insertions, deletions, or a combination thereof. Deletions may further include larger changes, such as deletions of a domain or exon. Other modifications of interest include additions, such as in epitope tagging, e.g., with the FLAG system, HA, green fluorescent proteins (GFP), etc.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-finction relationships of differentially expressed polypeptides, or to alter properties of the protein that affect its function or regulation (e.g., to provide polynucleotides or polypeptides enhanced or diminished in a selected activity).

Production of In vivo Models of Differentially Expressed Polynucleotide Function The subject nucleic acids can be used to generate transgenic, non-human animals or site specific gene modifications in cell lines. "Transgenic animals" encompasses genetically modified, non-human hosts having a deletion ("knock-out") of one or both alleles of a differentially expressed gene, or an introduced copy ("knock-in") of an endogenous or exogenous differentially expressed gene. "Transgenic animals" also encompasses conditional knock-outs and other transgenic animals altered for expression of a polynucleotide of the invention. Transgenic animals may be made through homologous recombination, where the normal locus of the particular gene of interest is altered, or may be made by random genomic integration or episomal maintenance of a nucleic acid construct into the host genome. The host animal may be of any suitable genus or species, particularly a mammal (e.g., rodents (mice, rats, etc.), cows, pigs, goats, horses, etc.

The modified cells or animals are useful in the study of differentially expressed gene function and regulation. For example, a series of small deletions and/or substitutions may be made in the host's native gene to determine the role of different exons in differentially expressed gene activity. Specific constructs of interest include anti-sense nucleic acid compositions, which will block gene expression, expression of dominant negative mutations, and over-expression of genes. Where a particular sequence is introduced, the introduced sequence may be either a complete or partial sequence of a gene native to the host, or may be a complete or partial sequence that is exogenous to the host animal, e.g., a human sequence. A detectable marker, such as lac Z, may be introduced into the locus, where upregulation of gene expression will result in an easily detected change in phenotype. One may also provide for expression of the differentially expressed gene or variants thereof in cells or tissues where it is not normally expressed, at levels not normally present in such cells or tissues, or at abnormal times of development.

Vectors for use in production of transgenic animals are known in the art (e.g., plasmids, retroviral vectors (as wells as vectors based on other animal viruses), YACs, etc. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

Transgenic animals may be produced according to methods well known in the art. For example, transgenic animals may be produced using embryonic stem (ES) cells. An ES cell line may be employed, or embryonic cells may be obtained freshly from a host, e.g., mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g., to determine the effect of a candidate drug on activity of the gene product of the differentially expressed gene.

Production of In vitro Models of Function of Differentially Expressed Genes

One can also use the compositions of the subject invention to produce in vitro models of differentially expressed gene function, where the format of such models can be readily determined by those of skill in the art. For example, the differentially expressed polynucleotides of the invention can be used in conjunction with in vitro cell lines to examine the effect of modification of expression (e.g., overexpression or inhibition of expression) of a selected polynucleotide of the invention. For example where a differentially expressed polynucleotide is substantially selectively underexpressed in a cancerous pancreatic cell, the in vitro expression system can use an appropriate cancerous pancreatic cell line to examine the effect of increasing expression of the polynucleotide. Where increasing expression the underexpressed polynucleotide in the cancerous cell line results in a desirable effect (e.g., inhibition of growth of the cell line, affect upon morphology, etc.), the differentially expressed polynucleotide is identified as corresponding to a gene that plays an important role in development or regulation of the cancerous phenotype, and thus may be useful as a therapeutic agent or target of a therapeutic agent.

Libraries and Computer-related Embodiments

A library of polynucleotides is a collection of sequence information, which information is provided in either biochemical form (e.g., as a collection of polynucleotide molecules), or in electronic form (e.g., as a collection of polynucleotide sequences stored in a computer-readable form, as in a computer system and/or as part of a computer program), where the sequence information of the polynucleotides serve as markers of a particular pancreatic disease. A marker of a pancreatic disease is a representation of a cellular product that is present either at an increased or decreased level relative to normal pancreatic cells. For example, a polynucleotide sequence in a library may be a polynucleotide that represents an mRNA, polypeptide, or other gene product encoded by the polynucleotide, that is either overexpressed or underexpressed in a cell affected by pancreatic disease relative to a normal (i.e., substantially disease-free) pancreatic cell.

The nucleotide sequence information of the library may be embodied in any suitable form, e.g., electronic or biochemical forms. For example, a library of sequence information embodied in electronic form includes an accessible computer data file that contains the representative nucleotide sequences of genes that are differentially expressed (e.g., overexpressed or underexpressed) as between, for example, i) a cancerous pancreatic cell and a normal pancreatic cell; ii) a cancerous pancreatic cell and a dysplastic pancreatic cell; iii) a cancerous pancreatic cell and a pancreatic cell affected by pancreatitis; iv) a pancreatic cell of an individual affected by diabetes (Type I or Type II ) and a normal pancreatic cell (e.g., unaffected by diabetes); and/or v) a dysplastic pancreatic cell relative to a normal pancreatic cell. Other combinations and comparisons of pancreatic cells of various disease will be readily apparent to the ordinarily skilled artisan. Biochemical embodiments of the library include a collection of nucleic acids that have the sequences of the genes in the library, where the nucleic acids may correspond to the entire gene in the library or to a fragment thereof, as described in greater detail below.

The differentially expressed polynucleotides of the library have nucleotide sequences of at least about 10 nt to about 100 nt, usually at least about 20 nt to 200 nt, and more usually at least about 50 nt to about 500 nt or more, up to about 300 nt to about 1,000 nt to about 1,500 nt of genes that are differentially expressed in pancreatic cells that are differentially affected by a disease or condition (e.g., cancer, dysplasia, pancreatitis, diabetes, normal, etc.). The polynucleotide libraries of the subject invention include sequence information of a plurality of polynucleotide sequences, where at least one of the polynucleotides has a sequence of any of SEQ ID NOS:1–6. By plurality is meant at least 2, usually at least 3 and may include all six of SEQ ID NOS:1–6. The length and number of polynucleotides in the library will vary with the nature of the library, e.g., if the library is an oligonucleotide array, a cDNA array, a computer database of the sequence information, etc.

Where the library is an electronic library, the nucleic acid sequence information can be present in a variety of media.

"Media" refers to a manufacture, other than an isolated nucleic acid molecule, that contains the sequence information of the present invention. Such a manufacture provides the genome sequence or a subset thereof in a form that can be examined by means not directly applicable to the sequence as it exists in a nucleic acid. For example, the nucleotide sequence of the present invention, e.g. the nucleic acid sequences of any of the polynucleotides of SEQ ID NOS:1–6, can be recorded on computer readable media, e.g. any medium that can be read and accessed directly by a computer. Such media include, but are not limited to: magnetic storage media, such as a floppy disc, a hard disc storage medium, and a magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present sequence information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

By providing the nucleotide sequence in computer readable form, the information can be accessed for a variety of purposes. Computer software to access sequence information is publicly available. For example the BLAST (Altschul et al., supra.) and BLAZE (Brutlag et al.(1993) *Comp. Chem.* 17:203–207) search algorithms on a Sybase system can be used identify open reading frames (ORFs) within the genome that contain homology to ORFs or proteins from other organisms.

As used herein, "a computer-based system" refers to the hardware means, software means, and data storage means used to analyze the nucleotide sequence information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present sequence information as described above, or a memory access means that can access such a manufacture.

"Search means" refers to one or more programs implemented on the computer-based system, to compare a target sequence or target structural motif with the stored sequence information. Search means are used to identify fragments or regions of the genome that match a particular target sequence or target motif. A variety of known algorithms are publicly known and commercially available, e.g. MacPattern (EMBL), BLASTN and BLASTX (NCBI). A "target sequence" can be any DNA or amino acid sequence of six or more nucleotides or two or more amino acids, preferably from about 10 to 100 amino acids or from about 30 to 300 nucleotide residues.

A "target structural motif," or "target motif," refers to any rationally selected sequence or combination of sequences in which the sequence(s) are chosen based on a three-dimensional configuration that is formed upon the folding of the target motif, or on consensus sequences of regulatory or active sites. There are a variety of target motifs known in the art. Protein target motifs include, but are not limited to, enzyme active sites and signal sequences. Nucleic acid target motifs include, but are not limited to, hairpin structures, promoter sequences and other expression elements such as binding sites for transcription factors.

A variety of structural formats for the input and output means can be used to input and output the information in the computer-based systems of the present invention. One format for an output means ranks fragments of the genome possessing varying degrees of homology to a target sequence or target motif. Such presentation provides a skilled artisan with a ranking of sequences and identifies the degree of sequence similarity contained in the identified fragment.

A variety of comparing means can be used to compare a target sequence or target motif with the data storage means to identify sequence fragments of the genome. A skilled artisan can readily recognize that any one of the publicly available homology search programs can be used as the search means for the computer based systems of the present invention.

As discussed above, the "library" of the invention also encompasses biochemical libraries of the differentially expressed polynucleotides of SEQ ID NOS:1–6, e.g., collections of nucleic acids representing these differentially expressed sequences. The biochemical libraries may take a variety of forms, e.g. a solution of cDNAs, a pattern of probe nucleic acids stably associated with a surface of a solid support, i.e. an array, and the like. Of particular interest are nucleic acid arrays in which one or more of SEQ ID NOS:1–6 is represented on the array. By array is meant a an article of manufacture that has at least a substrate with at least two distinct nucleic acid targets on one of its surfaces, where the number of distinct nucleic acids may be considerably higher, typically being at least 10 nt, usually at least 20 nt and often at least 25 nt. A variety of different array formats have been developed and are known to those of skill in the art, including those described in U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,895; 5,624,711; 5,639,603; 5,658,734; WO 93/17126; WO 95/11995; WO 95/35505; EP 742 287; and EP 799 897, the disclosures of which are herein incorporated by reference. The arrays of the subject invention find use in a variety of applications, including gene expression analysis, drug screening, mutation analysis and the like, as disclosed in the above listed patent documents.

In addition to the above nucleic acid libraries, analogous libraries of differentially expressed polypeptides are also provided, where the where the polypeptides of the library will represent at least a portion of the polypeptides encoded by SEQ ID NOS:1–6.

Diagnostic Applications

Also provided are methods of diagnosing disease states associated with expression of differentially expressed genes, e.g., based on observed levels of a differentially expressed polypeptide or the expression level of a differentially expressed gene in a biological sample of interest. In general, the diagnostic methods of the invention involve detection of a level or amount of a differentially expressed gene product in a test sample obtained from a patient suspected of having or being susceptible to a pancreatic disease (e.g., cancer, pancreatitis, diabetes, etc.), and comparing the detected levels to those levels found in normal cells (e.g., cells substantially unaffected by cancer) and/or other control cells (e.g., to differentiate a cancerous cell from a cell affected by dysplasia or pancreatitis). Furthermore, the severity of the disease may be assessed by comparing the detected levels of differentially expressed gene product with those levels detected in samples representing the levels of differentially gene product associated with varying degrees of severity of pancreatic cancer.

Diagnostic methods of the subject invention typically involve comparison of the abundance of a selected differentially expressed gene product in a sample of interest with that of a control to determine any relative differences in the expression of the gene product, where the difference may be measured qualitatively and/or quantitatively. The differences in expression are then correlated with the presence or absence of an abnormal expression pattern. A variety of different methods for determining the nucleic acid abundance in a sample are known to those of skill in the art, where particular methods of interest include those described in: Pietu et al. (1996) *Genome Res.* 6:492; Zhao et al. (1995) *Gene* 156:207; Soares , (1977) *Curr. Opin. Biotechnol.* 8: 542–546; Raval, (1994) *J. Pharmacol Toxicol Methods* 32:125; Chalifour et al. (1994) *Anal. Biochem* 216:299; Stolz et al., (1996) *Mol. Biotechnol.* 6:225; Hong et al., (1982) *Biosci. Reports* 2:907; and McGraw, (1984) *Anal. Biochem.* 143:298. Also of interest are the methods disclosed in WO 97/27317, the disclosure of which is herein incorporated by reference.

In general, diagnostic assays of the invention involve detection of a gene product of a the polynucleotide sequence (e.g., mRNA or polypeptide) that corresponds to a sequence set forth in any one of SEQ ID NOS:1–6. The patient from whom the sample is obtained can be apparently healthy, susceptible to pancreatic disease (e.g., as determined by family history or exposure to certain environmental factors), or can already be identified as having a condition in which altered expression of a gene product of the invention is implicated.

The level of a particular expression product of a polynucleotide sequence of the invention in a sample can be determined qualitatively or quantitatively. Quantitation can be accomplished, for example, by comparing the level of expression product detected in the sample with the amounts of product present in a standard curve. A comparison can be made visually or using a technique such as densitometry, with or without computerized assistance.

In the assays of the invention, the diagnosis may be determined based on detected gene product expression levels of a gene product encoded by at least one, preferably at least two or more, at least 3 or more, or at least 4 or more of the polynucleotides having a sequence set forth in SEQ ID NOS:1–6, and may involve detection of expression of genes corresponding to all 6 of SEQ ID NOS:1–6 and/or additional sequences that can serve as additional diagnostic markers and/or reference sequences. Where the diagnostic method is designed to detect the presence or susceptibility of a patient to pancreatic cancer, the assay preferably involves detection of a gene product encoded by a polynucleotide having the sequence of SEQ ID NO:2, which is overexpressed in pancreatic cancer. Where the diagnostic method is designed to detect the presence or susceptibility of a patient to pancreatic dysplasia, the assay preferably involves detection of at least one of the gene products encoded by a polynucleotide having the sequence of SEQ ID NOS:4 and 5, which are overexpressed in pancreatic dysplasia, and/or SEQ ID NOS:1 and 3, which are underexpressed in pancreatic dysplasia. Diagnosis of pancreatic cancer and/or pancreatic dysplasia can also involve the detection of the gene product encoded by a polynucleotide having the sequence set forth in SEQ ID NO:6, which is underexpressed in both pancreatic cancer and dysplasia.

Any of a variety of detectable labels can be used in connection with the various embodiments of the diagnostic methods of the invention. Suitable detectable labels include fluorochromes,(e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA)), radioactive labels, (e.g. $^{32}$P, $^{35}$S, $^{3}$H, etc.), and the like. The detectable label may involve a two stage systems (e.g., biotin-avidin, hapten-anti-hapten antibody, etc.)

Reagents specific for the polynucleotides and polypeptides of the invention, such as antibodies and nucleotide probes, can be supplied in a kit for detecting the presence of an expression product in a biological sample. The kit can also contain buffers or labeling components, as well as instructions for using the reagents to detect and quantify expression products in the biological sample. Exemplary embodiments of the diagnostic methods of the invention are described below in more detail.

Polypeptide Detection in Diagnosis

In one embodiment, the test sample is assayed for the level of a differentially expressed polypeptide. Diagnosis may be accomplished using any of a number of methods to determine the absence or presence or altered amounts of the differentially expressed polypeptide in the test sample. For example, detection may utilize staining of cells or histological sections with labeled antibodies, performed in accordance with conventional methods. Cells may be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody may be detectably labeled for direct detection (e.g., using radioisotopes, enzymes, fluorescers, chemiluminescers, and the like), or may be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding may be determined by various methods, including flow cytometry of dissociated cells, microscopy, radiography, scintillation counting, etc. Any suitable alternative methods can of qualitative or quantitative detection of levels or amounts of differentially expressed polypeptide may be used, for example ELISA, western blot, immunoprecipitation, radioimmunoassay, etc.

In general, the detected level of differentially expressed polypeptide in the test sample is compared to a level of the differentially expressed gene product in a reference or control sample, e.g., in a normal cell (negative control) or in a cell having a known disease state (positive control). For example, a higher level of expression of a polypeptide encoded by SEQ ID NO:2 relative to a level associated with a normal sample is indicative of the presence of pancreatic cancer in the patient from whom the sample is derived. A higher level of expression of a polypeptide encoded by SEQ ID NOS:4 or 5 relative to a level associated with a normal sample is indicative of the presence of pancreatic dysplasia, while detection of a lower level of expression of a polypeptide encoded by SEQ ID NOS:1 or 3 relative to a level associated with a normal sample is indicative of the presence of pancreatic dysplasia in the patient from whom the sample is derived. Detection of a lower level of the polypeptide encoded by SEQ ID NO:6 relative to a normal level is indicative of the presence of pancreatic cancer and/or dysplasia in the patient.

mRNA Detection

The diagnostic methods of the invention can also or alternatively involve detection of mRNA encoded by a gene corresponding to a differentially expressed polynucleotides of the invention. Any suitable qualitative or quantitative methods known in the art for detecting specific mRNAs can be used. mRNA can be detected by, for example, in situ hybridization in tissue sections, by reverse transcriptase-PCR, or in Northern blots containing poly A+ mRNA. One of skill in the art can readily use these methods to determine differences in the size or amount of mRNA transcripts between two samples. For example, the level of mRNA of the invention in a tissue sample suspected of being cancerous or dysplastic is compared with the expression of the mRNA in a reference sample, e.g., a positive or negative control sample (e.g., normal tissue, cancerous tissue, etc.).

In general, detection in the test sample of a higher level of mRNA expressed from a polynucleotide sequence having a sequence of SEQ ID NO:2, as compared to the normal tissue, indicates the presence of pancreatic cancerous cells in the suspect tissue. A higher level of mRNA having a sequence corresponding to a sequence of SEQ ID NOS:4 or 5, as compared to the normal tissue, indicates the presence dysplastic cells in the test sample. A lower level of the mRNA having a sequence corresponding to a sequence of SEQ ID NOS:1 or 3, as compared to the normal tissue, indicates the presence of dysplastic cells in the test sample. A lower level of niRNA having a sequence corresponding to a sequence of SEQ ID NO:6 is indicative of the presence of cancerous and/or dysplastic cells in the test sample. Any combinations of these sequences can be used in diagnosis.

Any suitable method for detecting and comparing mRNA expression levels in a sample can be used in connection with the diagnostic methods of the invention (see, e.g., U.S. Pat. No. 5,804,382). For example, mRNA expression levels in a sample can be determined by generation of a library of expressed sequence tags (ESTs) from the sample, where the EST library is representative of sequences present in the sample (Adams, et al., (1991) *Science* 252:1651). Enumeration of the relative representation of ESTs within the library can be used to approximate the relative representation of the gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al. (1995) *Science* 270:484). In short, SAGE involves the isolation of short unique sequence tags from a specific location within each transcript (e.g., a sequence of any one of SEQ ID NOS:1–6). The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. Nos. 5,776,683; and 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Use of a Single Gene in Diagnostic Applications

The diagnostic methods of the invention may also focus on the expression of a single differentially expressed gene. For example, the diagnostic method may involve detecting a differentially expressed gene, or a polymorphism of such a gene (e.g., a polymorphism in an coding region or control region), that is associated with disease. Disease-associated polymorphisms may include deletion or truncation of the gene, mutations that alter expression level and/or affect activity of the encoded protein, etc.

Changes in the promoter or enhancer sequence that may affect expression levels of an differentially gene can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express a differentially expressed gene may be used as a source of mRNA, which may be assayed directly or reverse transcribed into cDNA for analysis. The nucleic acid may be amplified by conventional techniques, such as the polymerase chain reaction (PCR), to provide sufficient amounts for analysis, and a detectable label may be included in the amplification reaction (e.g., using a detectably labeled primer or detectably labeled oligonucleotides) to facilitate detection. The use of the polymerase chain reaction is described in Saiki, et al. (1985), *Science* 239:487, and a review of techniques may be found in Sambrook, et al. (1989), *Molecular Cloning: A Laboratory Manual*, pp. 14.2–14.33. Alternatively, various methods are known in the art that utilize oligonucleotide ligation as a means of detecting polymorphisms, for examples see Riley et al. (1990), *Nucl. Acids Res.* 18:2887–2890; and Delahunty et al. (1996), *Am. J. Hum. Genet.* 58:1239–1246.

The sample nucleic acid, e.g. amplified or cloned fragment, is analyzed by one of a number of methods known in the art. The nucleic acid may be sequenced by dideoxy or other methods, and the sequence of bases compared to a selected sequence, e.g., to a wild-type sequence. Hybridization with the polymorphic or variant sequence may also be used to determine its presence in a sample (e.g., by Southern blot, dot blot, etc.). The hybridization pattern of a polymorphic or variant sequence and a control sequence to an array of oligonucleotide probes immobilized on a solid support, as described in U.S. Pat. No. 5,445,934, or in WO 95/35505, may also be used as a means of identifying polymorphic or variant sequences associated with disease. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in an differentially expressed gene may be based on the functional or antigenic characteristics of the protein. Protein truncation assays are useful in detecting deletions that may affect the biological activity of the protein. Various immunoassays designed to detect polymorphisms in proteins may be used in screening. Where many diverse genetic mutations lead to a particular disease phenotype, functional protein assays have proven to be effective screening tools. The activity of the encoded protein may be determined by comparison with the wild-type protein.

Pattern Matching in Diagnosis Using Arrays

In another embodiment, the diagnostic methods of the invention involve detection of expression of a selected set of genes in a test sample to produce a test expression pattern (TEP). The TEP is compared to a reference expression pattern (REP), which is generated by detection of expression of the selected set of genes in a reference sample (e.g., a positive or negative control sample). The selected set of genes includes at least one of the differentially expressed genes of the invention, which genes correspond to the polynucleotide sequences of SEQ ID NOS:1–6.

REPs can be generated in a variety of ways according to methods well known in the art. For example, REPs can be generated by hybridizing a control sample to an array having a selected set of polynucleotides (particularly a selected set of differentially expressed polynucleotides), acquiring the hybridization data from the array, and storing the data in a format that allows for ready comparison of the REP with a TEP. Alternatively, all expressed sequences in a control sample can be isolated and sequenced, e.g., by isolating mRNA from a control sample, converting the mRNA into cDNA, and sequencing the cDNA. The resulting sequence information roughly or precisely reflects the identity and relative number of expressed sequences in the sample. The sequence information can then be stored in a format (e.g., a computer-readable format) that allows for ready comparison of the REP with a TEP. The REP can be normalized prior to or after data storage, and/or may be processed to selectively remove sequences of expressed genes that are of less interest or that may complicate analysis (e.g., some or all of the sequences associated with housekeeping genes may be eliminated from the REP data).

TEPs can be generated in a manner similar to REPs, e.g., by hybridizing a test sample to an array having a selected set of polynucleotides, particularly a selected set of differentially expressed polynucleotides, acquiring the hybridization data from the array, and storing the data in a format that allows for ready comparison of the TEP with a REP. The REP and TEP to be used in a comparison may be generated simultaneously, or the TEP may be compared to previously generated and stored REPs.

In one embodiment of the invention, comparison of a TEP with a REP involves hybridizing a test sample with a reference array, where the reference array has one or more reference sequences for use in hybridization with a sample. The reference sequences include all, at least one of, or any subset of the differentially expressed polynucleotides listed in Table 1. Hybridization data for the test sample is acquired, the data normalized, and the produced TEP compared with a REP generated using an array having the same or similar selected set of differentially expressed polynucleotides. Probes that correspond to sequences differentially expressed between the two samples will show decreased or increased hybridization efficiency for one of the samples relative to the other.

Reference arrays may be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with a reference arrays are also well known in the art. For example, the polynucleotides of the reference and test samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that may be used in the subject methods is described in U.S. Pat. No. 5,631,734. A scanning laser microscope is described in Shalon et al. (1996) *Genome Res.* 6:639. A scan, using the appropriate excitation line, is performed for each fluorophore used. The digital images generated from the scan are then combined for subsequent analysis. For any particular array element, the ratio of the fluorescent signal from one sample (e.g., a test sample) is compared to the fluorescent signal from another sample (e.g., a reference sample), and the relative signal intensity determined.

Methods for analyzing the data collected from hybridization to arrays are well known in the art. For example, where detection of hybridization involves a fluorescent label, data analysis may include the steps of determining fluorescent intensity as a function of substrate position from the data collected, removing outliers, i.e. data deviating from a predetermined statistical distribution, and calculating the relative binding affinity of the targets from the remaining data. The resulting data may be displayed as an image with the intensity in each region varying according to the binding affinity between targets and probes.

In general, the test sample is classified as having a gene expression profile corresponding to that associated with a disease or non-disease state (e.g., pancreatic cancer, pancreatic dysplasia, pancreatitis, diabetes, normal, etc.) by comparing the TEP generated from the test sample to one or more REPs generated from reference samples (e.g., from samples associated with pancreatic cancer, pancreatic dysplasia, pancreatitis, diabetes, normal, etc.). The criteria for a match or a substantial match between a TEP and a REP include expression of the same or substantially the same set of reference genes, as well as expression of these reference genes at substantially the same levels (e.g., no significant difference between the samples for a signal associated with a selected reference sequence after normalization of the samples, or at least no greater than about 25% to about 40% difference in signal strength for a given reference sequence. In general, a pattern match between a TEP and a REP includes a match in expression, preferably a match in qualitative or quantitative expression level, of at least one of, all or any subset of the differentially expressed genes of the invention as represented by SEQ ID NOS:1–6.

Pattern matching may be performed manually, or may be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

Screening Assays

The differentially expressed polynucleotides and polypeptides of the invention can be used in a screening assay designed to identify agents that modulate activity of the differentially expressed gene product, e.g., by modulating expression (e.g., enhancing or inhibiting expression), by modulating polypeptide activity (e.g., enhancing or inhibiting a biological activity), and the like. The screening methods will typically be assays that provide for qualitative and/or quantitative measurements of biological activity in the presence of a particular candidate therapeutic agent. For example, the assay may measure activity a polypeptide in the presence and absence of a candidate inhibitor agent, or may examine the effect of a candidate agent upon expression of a selected polynucleotide.

The screening method may be an in vitro or in vivo format, where both formats are readily developed by those of skill in the art. Depending on the particular method, one or more of, usually one of, the components of the screening assay may be detectably labeled, e.g. using a fluorescent or radioactive tag, or a member of a multicomponent signal producing system, e.g. biotin for binding to an enzyme-streptavidin conjugate in which the enzyme is capable of converting a substrate to a chromogenic product. A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

A variety of different candidate agents may be screened in such screening assays. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Drug screening may be performed using an in vitro model, a genetically altered cell or animal, or purified differentially expressed polypeptide to facilitate identification of ligands or substrates that bind to, modulate or mimic the action of a differentially expressed polypeptide. Areas of particular interest include the development of cancer treatments, metastasis, etc. Drug screening may also be performed for identification of agents that provide a replacement for or increase the function of a differentially expressed polypeptide that is underexpressed in abnormal cells. Conversely, agents that inhibit function of a differentially expressed polypeptide that is overexpressed in abnormal cells are predicted to inhibit the process of disease (e.g. oncogenesis). Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions.

Therapeutic Compositions

The differentially expressed polynucleotides and polypeptides of the invention may be used as therapeutic agents. Generally, therapeutic agents and methods of the invention are premised on modulating the activity of an differentially expressed gene product (e.g., polypeptide), where such modulation is accomplished by either enhancing or inhibiting gene expression or polypeptide activity. The active agent may be a variety of different compounds, including a naturally occurring or synthetic small molecule compound, an antibody, fragment or derivative thereof, an antisense composition, and the like as exemplified below. Active agents described herein as therapeutic agents may also find use in non-therapeutic applications, e.g., in animal models of disease, as reagents, etc.

Where the therapeutic agent is used to decrease expression of the polynucleotides of the invention, the agent can decrease expression of the polynucleotide by at least about 50%, usually at least about 60% to 70%, and may facilitate a decrease in expression of at least about 80% or 90% to 95%, up to about 99% to 100%. The effectiveness of the mechanism chosen to alter expression of the polynucleotide can be assessed using methods well known in the art, such as hybridization of nucleotide probes to mRNA of the polynucleotide, quantitative RT-PCR, or detection of a protein using specific antibodies of the invention.

Alternatively, agents for expression modulation can be designed to increase expression of a differentially expressed polynucleotide. Increasing expression of such polynucleotides may also be useful to, for example, decrease the growth rate of pancreatic cancer cells and cancer cells of other tissue origin, where the particular polynucleotide is down-regulated in cancer cells. Within an expression construct, the polynucleotide segment is oriented in the sense direction and is located downstream from the promoter. Transcription of the polynucleotide segment initiates at the promoter. The expression construct can be introduced into cells along with a pharmaceutically acceptable carrier to decrease the growth rate of cancer cells or ameliorate other abnormal characteristics. Expression of the polynucleotide. sequence can be monitored by detecting production of mRNA which hybridizes to the delivered polynucleotide or by detecting protein encoded by the delivered polynucleotide.

Exemplary agents for modulation of expression of differentially expressed polynucleotides are provided below.

Small molecule compounds. Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Active agents for modulation of activity also include antibodies that specifically bind a differentially expressed polypeptide of the invention.

Antisense molecules. Antisense molecules can be used to down-regulate expression of genes in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides can be composed of deoxyribonucleotides, ribonucleotides, or a combination of both. Oligonucleotides can be synthesized manually or by an automated synthesizer, e.g., by covalently linking the 5' end of one nucleotide with the 3' end of another nucleotide with phosphodiester or non-phosphodiester internucleotide linkages such as alkylphosphonates, phosphorothioates, phosphorodithioates, alkylphosphonothioates, alkylphosphonates, phosphoramidates, phosphate esters, carbanates, acetamidate, carboxymethylesters, carbonates, and phosphate triesters. See Brown (1994) *Meth. Mol. Biol.* 20:1; Sonveaux (1994) *Meth. Mol. Biol.* 26:1; Uhlmann et al. (1990) *Chem. Rev.* 90:543. Antisense oligonucleotides may also be chemically synthesized by methods known in the art (see Wagner et al. (1993), supra, and Milligan et al., supra.)

Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Ribozymes. As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56. Ribozymes and their use to decrease expression of a selected gene is described in, for example, Cech (1987) *Science* 236:1532; Cech (1990) *Ann. Rev. Biochem.* 59:543; Cech (1992) *Curr. Opin. Struct. Biol.* 2:605; Couture et al. (1996) *Trends Genet.* 12:510; and U.S. Pat. No. 5,641,673). As per U.S. Pat. No. 5,641,673, ribozymes can be engineered so that their expression occurs in response to factors that also induce expression of a polynucleotides of the invention. The ribozyme can also be engineered to provide an additional level of regulation, so that destruction of RNA occurs only when both the ribozyme and the corresponding gene are induced in the cells.

Ribozymes of the invention can be introduced into cells as part of a DNA construct, as is known in the art. The DNA construct can also include transcriptional regulatory elements, such as a promoter element, an enhancer or UAS element, and a transcriptional terminator signal, for controlling the transcription of the ribozyme in the cells. Mechanical methods, such as microinjection, liposome-mediated transfection, electroporation, gene gun, or calcium phosphate precipitation, can be used to introduce the ribozyme-containing DNA construct into cells whose division it is desired to decrease, as described above. Alternatively, if it is desired that the DNA construct be stably retained by the cells, the DNA construct can be supplied on a plasmid and maintained as a separate element or integrated into the genome of the cells, as is known in the art.

Antibodies. Expression of the polynucleotides of the invention can also be decreased by delivering polyclonal, monoclonal, or single chain antibodies that specifically bind to polypeptides expressed from the polynucleotide sequences as shown in SEQ ID NOS:1–6. Antibodies specific to these proteins bind to the protein and prevent the protein from functioning in the cell. Blocking protein expression or function is useful for preventing, reducing the effects of, or curing pancreatic disease.

Formulations. As mentioned above, an effective amount of the active agent is administered to the host, where "effective amount" means a dosage sufficient to produce a desired result, where the desired result in the desired modulation, e.g. enhancement, reduction, of the target protein activity.

The active agent can be incorporated into a variety of formulations for therapeutic administration. More particularly, the agents of the present invention can be formulated into pharmaceutical compositions by combination with appropriate, pharmaceutically acceptable carriers, adjuvants, or diluents (e.g., liquids, such as water, saline, glycerol, and ethanol), as well as substances such as wetting agents, emulsifying agents, or pH buffering agents, tonicity adjusting agents, stabilizers, wetting agents and the like. Liposomes, such as those described in U.S. Pat. No. 5,422,120, WO 95/13796, WO 91/14445, or EP 524,968 B1, can also be used as a carrier for the therapeutic composition. The compositions of the present invention may be formulated into pharmaceutical preparations in solid, semi-solid, liquid or gaseous forms, such as tablets, capsules, powders, granules, ointments, solutions, suppositories, injections, inhalants and aerosols. Pharmaceutically acceptable carriers are well known to those in the art. Such carriers include, but are not limited to, large, slowly metabolized macromolecule, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates.

Administration and dosage. Administration of the agents can be achieved in various ways, including oral, buccal, rectal, parenteral, intraperitoneal, intradermal, transdermal, intratracheal, etc., administration. In pharmaceutical dosage forms, the agents may be administered in the form of their pharmaceutically acceptable salts, or they may also be used alone or in appropriate association, as well as in combination, with other pharmaceutically active compounds. The methods and excipients described herein are merely exemplary and are in no way limiting.

The differentially expressed polynucleotides can be formulated for use in gene therapy to treat disorders associated with gene defects. Expression vectors, which generally have an expression cassette having convenient restriction sites located near a promoter sequence for operable insertion of a polynucleotide of interest, may be used to introduce the differentially expressed gene into a cell. The expression vectors may be provided in a variety of forms (e.g. plasmid; retrovirus, e.g., lentivirus; adenovirus; and the like). Following introduction into the cell, the vectors may be transiently or stably maintained either as an episome or as a genomic integrant, usually for a period of at least about one day, more usually for a period of at least about several days to several weeks.

Typically, a therapeutic composition is prepared as an injectable, either as a liquid solution or suspension; however, solid forms suitable for solution in, or suspension in, liquid vehicles prior to injection can also be prepared. A composition can also be formulated into an enteric coated tablet or gel capsule according to known methods in the art, such as those described in U.S. Pat. No. 4,853,230, EP 225,189, AU 9,224,296, and AU 9,230,801. In general, the agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be utilized in aerosol formulation to be administered via inhalation. The compounds of the present invention can be formulated into pressurized acceptable propellants such as dichlorodifluoromethane, propane, nitrogen and the like. Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Kits with unit doses of a therapeutic agent of the invention, usually in oral or injectable doses, are provided. In such kits, in addition to the containers containing the unit doses will be an informational package insert describing the use and attendant benefits of the drugs in treating pathological condition of interest.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Administration of the therapeutic agents of the invention can include systemic methods of delivery, as well as local administration. Various methods can be used to administer a therapeutic composition directly to a specific site in the body. For treatment of tumors, for example, a small tumor or metastatic lesion can be located and a therapeutic composition injected several times in several different locations within the body of the tumor. Alternatively, arteries which serve a tumor can be identified, and a therapeutic composition injected into such an artery, in order to del! ver the composition directly into the tumor.

A tumor which has a necrotic center can be aspirated and the composition injected directly into the now empty center of the tumor. A therapeutic composition can be directly administered to the surface of a tumor, for example, by topical application of the composition. X-ray imaging can be used to assist in certain of the above delivery methods. Combination therapeutic agents, including a polypeptide, polynucleotide, antibody, and/or other therapeutic agents, can be administered simultaneously or sequentially.

Receptor-mediated targeted delivery can be used to deliver therapeutic compositions containing polynucleotides, proteins, antibodies, ribozymes, or antisense oligonucleotides of the invention to specific tissues. Receptor-mediated delivery techniques are described in, for example, Findeis et al. (1993) *Trends Biotechnol.* 11:202; Chiou et al. (1994), *Gene Therapeutics: Methods And Applications of Direct Gene Transfer* (J. A. Wolff, ed.); Wu et al. (1988), *J. Biol. Chem.* 263:62; Wu et al., (1994) *J. Biol. Chem.* 269:542; Zenke et al. (1990) *Proc. Natl. Sci. U.S.A.* 87:3655; Wu et al. (1991) *J. Biol. Chem.* 266:338.

Alternatively, therapeutic compositions can be introduced into human cells ex vivo, and the cells then replaced into the human. Cells can be removed from a variety of locations including, for example, from a selected tumor or from an affected organ. In addition, a therapeutic composition can be inserted into non-affected cells, for example, dermal fibroblasts or peripheral blood leukocytes. If desired, particular fractions of cells such as a T cell subset or stem cells can also be specifically removed from the blood (see, for example, PCT WO 91/16116). The removed cells can then be contacted with a therapeutic composition utilizing any of the above-described techniques, followed by the return of the cells to the human, preferably to or within the vicinity of a tumor or other site to be treated. The methods described above can additionally comprise the steps of depleting fibroblasts or other non- contaminating tumor cells subsequent to removing tumor cells from a human, and/or the step of inactivating the cells, for example, by irradiation.

Both the dosage and means of administration can be determined based on a variety of factors such as the specific qualities of the therapeutic composition, the condition, age, and weight of the patient, the progression of the disease, and other relevant factors. If the composition contains protein, polypeptide, or antibody, effective dosages of the composition are in the range of about 5 pg to about 50 mg/kg of patient body weight, about 50 pg to about 5 mg/kg, about 100 pg to about 500 mg/kg of patient body weight, and about 200 to about 250 pg/kg. Those of skill in the art will readily appreciate that dose levels can vary as a function of the specific compound, the severity of the symptoms and the susceptibility of the subject to side effects. Preferred dosages for a given compound and for a given disease or condition are readily determinable by those of skill in the art by a variety of means.

Therapeutic compositions for use in gene therapy applications containing a differentially expressed polynucleotide of the invention can be administered in a range of about 100 ng to about 200 mg of DNA for local administration in a gene therapy protocol. Concentration ranges of about 500 ng to about 50 mg, about 1 pg to about 2 mg, about 5 pg to about 500 pg, and about 20 pg to about 100 pg of DNA can also be used during a gene therapy protocol. A variety of factors, such as method of action and efficacy of transformation and expression, will affect the dosage required for ultimate efficacy. Where greater expression is desired over a larger area of tissue, larger amounts of polynucleotides or the same amounts re- administered in a successive protocol of administrations, or several administrations to different adjacent or close tissue portions of, for example, a tumor site, can be used to effect a positive therapeutic outcome. In all cases, routine experimentation in clinical trials will determine specific ranges for optimal therapeutic effect.

Diseases amenable to therapy. The subject methods find use in the treatment of a variety of different conditions involving differentially expressed genes, including, for example, insufficient or hypo-protein activity and hyper-protein activity. In general, the subject methods and compositions are useful where the modulation of expression or a function of a differentially expressed gene product is desired. By "treatment" is meant that at least an amelioration of the symptoms associated with the condition afflicting the host, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalian, including the orders carnivore (e.g., dogs and cats), rodentia (e.g., mice, guinea pigs, and rats), and primates (e.g., humans, chimpanzees, and monkeys), where "treatment" in the context of non-human hosts can involve the use of the subject compositions and methods in animal models of disease. Of particular interest is the treatment of human host.

Use of the therapeutic compositions and methods of the invention in treating pancreatic cancer and pancreatic dysplasia is of particular interest. The therapeutic compositions may also find use in treatment of other types of cancers such as: bone cancer; brain tumors; breast cancer; endocrine system cancers, such as cancers of the thyroid, pituitary, and adrenal glands and the pancreatic islets; gastrointestinal cancers, such as cancer of the anus, colon, esophagus, gallbladder, stomach, liver, and rectum; genitourinary cancers such as cancer of the penis, prostate and testes; gynecological cancers, such as cancer of the ovaries, cervix, endometrium, uterus, fallopian tubes, vagina, and vulva; head and neck cancers, such as hypopharyngeal, laryngeal, oropharyngeal cancers, lip, mouth and oral cancers, cancer of the salivary gland, cancer of the digestive tract and sinus cancer; leukemia; lymphomas including Hodgkin's and non-Hodgkin's lymphoma; metastatic cancer; myelomas; sarcomas; skin cancer; urinary tract cancers including bladder, kidney and urethral cancers; and pediatric cancers, such as pediatric brain tumors, leukemia, lymphomas, sarcomas, liver cancer and neuroblastorna and retinoblastoma.

ATCC Deposits

The following plasmids were deposited as a bacterial culture with plasmid cDNA on Sep. 25, 1998 with the American Type Culture Collection, 10801 University Boulevard, Manassas, Va. 20110-2209, USA (ATCC) as ATCC accession no. 98896:

1) Clone HX2134-4 (containing an insert corresponding to SEQ ID NO:1),
2) Clone HX2144-1 (containing an insert corresponding to SEQ ID NO:2);
3) Clone HX2145-3 (containing an insert corresponding to SEQ ID NO:3);
4) Clone HX2162-3 (containing an insert corresponding to SEQ ID NO:4);
5) Clone HX2166-6 (containing an insert corresponding to SEQ ID NO:5); and
6) Clone HX2192-1 (containing an insert corresponding to SEQ ID NO:6).

The deposit was made under the conditions specified by the Budapest Treaty on the international recognition of the deposit of microorganisms (Budapest Treaty). Constructs and polynucleotides sequences equivalent to and/or substantially equivalent to the deposited material are also considered to be within the scope of this invention. Availability of the deposited material is not to be construed as a license to practice the invention in contravention of the rights granted under the authority of any government in accordance with its patent laws.

Each of the above clones was transfected into separate bacterial cells, and were deposited as a pool of equal mixtures of all six clones in this composite deposit. Each clone can be removed from the vector in which it was deposited by EcoRI to produce the appropriately sized 0.5 kb–1.0 kb fragment for the clone. Particular clones can be obtained from the composite deposit using methods well known in the art. For example, a bacterial cell containing a particular clone can be identified by isolating single colonies on an appropriate bacterial media containing ampicillin, and identifying colonies containing the specific clone through standard colony hybridization techniques, using an oligonucleotide probe or probes designed to specifically hybridize to a sequence of one of SEQ ID NOS:1–6. The probe should be designed to have a $T^m$ of approximately 80° C. (assuming 2° C. for each A or T and 4° C. for each G or C). Positive colonies can then be picked, grown in culture, and the recombinant clone isolated.

EXAMPLES

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

Example 1

A family was identified that had several members who had been diagnosed with pancreatic cancer. The family members also have a form of diabetes. The pathological features of disease in the family included progression from normal to metaplasia to dysplasia to cancer. Tissues were obtained from a member of the family diagnosed with pancreatic cancer and from a member of the family diagnosed with dysplasia of pancreatic cells, and primary cultures of ductal cells prepared according to methods well known in the art. Tissue was also obtained from an unrelated person who was diagnosed with pancreatitis, and from an unrelated person who had a normal pancreas, and primary cultures of ductal cells prepared according to methods well known in the art.

The Genomyx HIEROGLYPH™ mRNA profile kit for differential display analysis was used according to the manufacturer's instructions to identify genes that are differentially expressed in the various samples relative to one another. Briefly, mRNA was isolated from the primary ductal cell cultures, and subjected to reverse transcriptase polymerase chain reaction (PCR). The resulting cDNA was subjected to a differential display in which the cDNA from each of the samples were compared on a gel.

The cDNA fragment pattern in each sample was manually compared to the cDNA fragment pattern in every other sample on the gel. Those bands representing differentially expressed gene products (e.g., bands associated with relatively more or less cDNA in one sample relative to another) were cut from the gel, amplified, cloned, and sequenced. The following polynucleotide sequences (SEQ ID NOS:1–6) of cDNA fragments isolated from six such differentially displayed cDNA fragments were identified as being differentially regulated in pancreatic disease.

TABLE 1

Results of Differential Display

| SEQ ID NO. | Clone Name | Sequence Length (bp) | Results |
|---|---|---|---|
| 1 | HX2134-4 | 676 | Expression decreased in dysplasia only |
| 2 | HX2144-1 | 544 | Expression increased in cancer only |
| 3 | HX2145-3 | 432 | Expression decreased in dysplasia only |
| 4 | HX2162-3 | 493 | Expression increased in dysplasia only |
| 5 | HX2166-6 | 418 | Expression increased in dysplasia only |
| 6 | HX2192-1 | 1063 | Expression decreased in dysplasia and cancer |

The identification of these differentially expressed polynucleotides, as well as the tion of the relative levels of expression of the represented differentially expressed genes e disease states of pancreatic cancer and dysplasia, indicates that the gene products of the differentially expressed polynucleotides and genes can serve as markers of these disease where the markers can be used either singly or in combination with one another. Examination of expression of one or more of these differentially expressed polynucleotides can used in classifying the cell from which the polynucleotides are derived as, for example, cancerous, dysplastic, or normal, and can further be used in diagnosis of the subject from the cell sample was derived. Use of all or a subset of the differentially expressed polynucleotides as markers will increase the sensitivity and the accuracy of the diagnosis.

Example 2
Sequencing and Analysis of Differentially Expressed Polynucleotides

The sequences of the differentially expressed polynucleotides identified in Example 1 (SEQ ID NOS:1–6) were used as query sequences in the GenBank and dbEST public databases to identify possible homologous sequences. The search was performed using the BLAST program, with default settings. All six sequences were novel, i.e., no sequence present in the databases searched contained a sequence having the contiguous nucleotide sequence set forth in any of SEQ ID NOS:1–6. Moreover, each of the polynucleotides contained stretches of contiguous nucleotides for which no homologous sequence was identified. A summary of these wholly unique sequences, referred to herein as identifying sequences, is provided in Table 2 below.

TABLE 2

Identifying sequences of the differentially expressed genes of the invention.

| SEQ ID NO: | Identifying Sequences (numbering refers to nucleotide position in Sequence Listing) |
|---|---|
| 1 | 1–304; 533–571 |
| 2 | 1–62; 102–139; 183–544 |
| 3 | 1–41; 62–182; 216–281; 319–432 |
| 4 | 1–13; 32–137; 156–236; 255–429; 453–493 |
| 5 | 1–101; 408–418 |
| 6 | 327–444; 640–997; 1018–1063 |

The identifying sequences above represent exemplary minimal, contiguous nucleotides sequences of the differentially expressed polynucleotides than can be used in identification or detection of the corresponding differentially expressed genes described herein.

Example 3
Fabricating a DNA Array Using Polynucleotides Differentially Expressed in Pancreatic Cells A DNA array is made by spotting DNA fragments onto glass microscope slides that are pretreated with poly-L-lysine. Spotting onto the array is accomplished by a robotic arrayer. The DNA is cross-linked to the glass by ultraviolet irradiation, and the free poly-L-lysine groups are blocked by treatment with 0.05% succinic anhydride, 50% 1-methyl-2-pyrrolidinone and 50% borate buffer.

The spots on the array are oligonucleotides synthesized on an ABI automated synthesizer. Each spot is one of the polynucleotides of SEQ ID NOS:1–6, each of which correspond to a gene that is differentially expressed in pancreatic cells according to varying disease states (e.g., overexpressed or underexpressed in cancerous, dysplastic, pancreatitis, and/or diabetic pancreatic cells). The polynucleotides may be present on the array in any of a variety of combinations or subsets. Some internal standards and negative control spots including non-differentially expressed sequences and/ or bacterial controls are included. mRNA from patient samples is isolated, the mRNA used to produce cDNA, amplified and subsequently labeled with fluorescent nucleotides as follows: isolated mRNA is added to a standard PCR reaction containing primers (100 pmoles each), 250 uM nucleotides, and 5 Units of Taq polymerase (Perkin Elmer). In addition, fluorescent nucleotides (Cy3-dUTP (green fluorescence) or Cy5-dUTP (red fluorescence), sold by Amersham) are added to a final concentration of 60 uM. The reaction is carried out in a Perkin Elmer thermocycler (PE9600) for 30 cycles using the following cycle profile: 92° C. for 30 seconds, 58° C. for 30 seconds, and 72° C. for 2 minutes. Unincorporated fluorescent nucleotides are removed by size exclusion chromatography (Microcon-30 concentration devices, sold by Amicon).

Buffer replacement, removal of small nucleotides and primers and sample concentration is accomplished by ultrafiltration over an Amicon microconcentrator-30 (mwco=30, 000 Da) with three changes of 0.45 ml TE. The sample is reduced to 5 µl and supplemented with 1.4 µl 20×SSC and 5 µg yeast tRNA. Particles are removed from this mixture by filtration through a pre-wetted 0.451µ microspin filter (Ultrafree-MC, Millipore, Bedford, Mass.). SDS is added to a 0.28% final concentration. The fluorescently-labeled cDNA mixture is then heated to 98° C. for 2 min., quickly cooled and applied to the DNA array on a microscope slide. Hybridization proceeds under a coverslip, and the slide assembly is kept in a humidified chamber at 65° C. for 15 hours.

The slide is washed briefly in 1×SSC and 0.03% SDS, followed by a wash in 0.06% SSC. The slide is kept in a humidified chamber until fluorescence scanning was done. Fluorescence scanning and data acquisition are then accomplished using any of a variety of suitable methods well known in the art. For example, fluorescence scanning is set for 20 microns/pixel and two readings are taken per pixel. Data for channel 1 is set to collect fluorescence from Cy3 with excitation at 520 nm and emission at 550–600 nm. Channel 2 collects signals excited at 647 nm and emitted at 660–705 nm, appropriate for CyS. No neutral density filters are applied to the signal from either channel, and the photomultiplier tube gain is set to 5. Fine adjustments are then made to the photomultiplier gain so that signals collected from the two spots are equivalent.

The data acquired from the scan of the array is then converted to any suitable form for analysis. For example, the data may be analyzed using a computer system, and the data may be displayed in a pictoral format on a computer screen, where the display shows the array as a collection of spots, each spot corresponding to a location of a different polynucleotide on the array. The spots vary in brightness according to the amount of fluorescent probe associated with the spot, which in turn is correlated with an amount of hybridized cDNA in the sample. The relative brightness of the spots on the array can be compared with one another to determine their relative intensities, either qualitatively or quantitatively.

The display of spots on the array, along with their relative brightness, provides a test sample pattern. The test sample pattern can be then compared with reference array patterns associated with positive and negative control samples on the same array, e.g., an array having polynucleotides in substantially the same locations as the array used with the test sample. The reference array patterns used in the comparison can be array patterns generated using samples from normal pancreas cells, cancerous pancreas cells, pancreatitis-associated pancreas cells, diabetic pancreas cells, and the like. A substantial or significant match between the test array pattern and a reference array pattern is indicative of a disease state of the patient from whom the test sample was obtained.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated polynuclecotide comprising the nucleotidc sequence of an insert contained in clone HX2134-4 corresponding to SEQ ID NO:1.

2. An isolated polynucleotide comprising the nucleotide sequence of an insert contained in clone HX2144-1 corresponding to SEQ ID NO:2.

3. An isolated polynucleotide comprising the nucleotide sequence of an insert contained in clone HX2145-3 corresponding to SEQ ID NO:3.

4. An isolated polynucleotide comprising the nucleotide sequence of an insert contained in clone HX2162-3 corresponding to SEQ ID NO:4.

5. An isolated polynucleotide comprising the nucleotide sequence of an insert contained in clone HX2166-6 corresponding to SEQ ID NO:5.

6. An isolated polynucleotide comprising the nucleotide sequence of an insert contained in clone HX2191-1 corresponding to SEQ ID NO:6.

* * * * *